United States Patent
Foster et al.

(10) Patent No.: US 8,389,013 B2
(45) Date of Patent: Mar. 5, 2013

(54) PROCESS FOR PRODUCING PARTICLES VIA ATOMIZED RAPID INJECTION FOR SOLVENT EXTRACTION

(75) Inventors: Neil Russell Foster, New South Wales (AU); Roderick Peng Tze Sih, Singapore (SG)

(73) Assignee: Newsouth Innovations PTY Limited, New South Wales (AU)

( * ) Notice: Subject to any disclaimer, the term of this patent is extended or adjusted under 35 U.S.C. 154(b) by 402 days.

(21) Appl. No.: 12/444,490

(22) PCT Filed: Oct. 5, 2007

(86) PCT No.: PCT/AU2007/001515
§ 371 (c)(1),
(2), (4) Date: Feb. 10, 2010

(87) PCT Pub. No.: WO2008/040094
PCT Pub. Date: Apr. 10, 2008

(65) Prior Publication Data
US 2010/0144670 A1    Jun. 10, 2010

(30) Foreign Application Priority Data
Oct. 6, 2006   (AU) .............................. 2006905571

(51) Int. Cl.
*A61K 9/14*    (2006.01)
*A61K 31/00*   (2006.01)
*B29B 9/10*    (2006.01)

(52) U.S. Cl. .................. 424/489; 264/5; 264/11; 264/12

(58) Field of Classification Search .................. None
See application file for complete search history.

(56) References Cited

U.S. PATENT DOCUMENTS

| 6,576,262 B1 * | 6/2003 | Hanna et al. | 424/489 |
| 6,596,206 B2 * | 7/2003 | Lee | 264/9 |
| 2006/0078619 A1 * | 4/2006 | Woo et al. | 424/489 |

OTHER PUBLICATIONS

Fischer et al. (Journal of Chemical Thermodynamics, 33, Published 2001, pp. 1285 and 1299).*
Torell et al. (Conversions for commonly used weights and measurements, Published Jun. 20, 2003).*
PCT International Search Report, PCT Application No. PCT/AU2007/001515, Nov. 15, 2007, 3 pages.
PCT Written Opinion, PCT Application No. PCT/AU2007/001515, Nov. 15, 2007, 4 pages.

* cited by examiner

*Primary Examiner* — Richard Schnizer
*Assistant Examiner* — Alma Pipic
(74) *Attorney, Agent, or Firm* — Fenwick & West LLP

(57) ABSTRACT

A process for producing particles of a substance is described wherein a solution of the substance in a solvent is delivered in at least one shot into a supercritical fluid. The supercritical fluid is a non-solvent for the substance and is miscible with the solvent. Particles of the substance distributed in a mixture of the solvent and the supercritical fluid are formed.

18 Claims, 15 Drawing Sheets

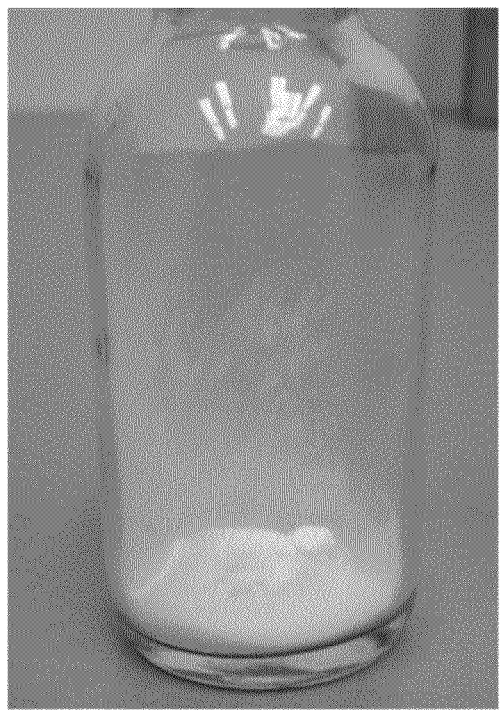
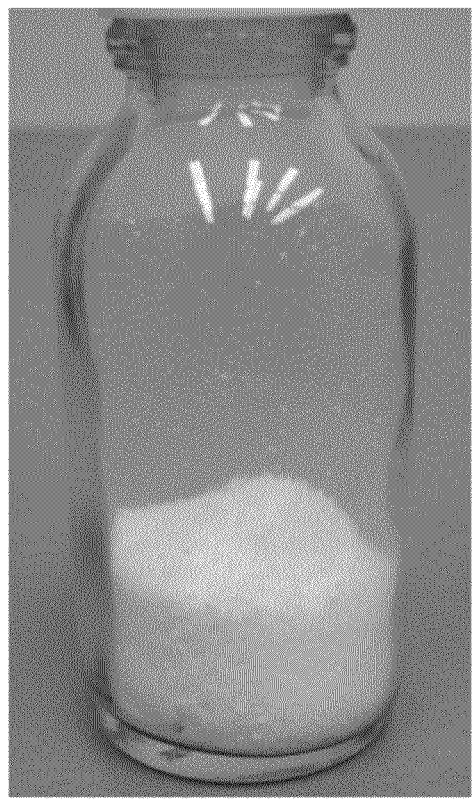
Fig. 7

MASTERSIZER

Result Analysis Report

| | | |
|---|---|---|
| Sample Name: 080806 - Average | SOP Name: | Measured: Thursday, August 17, 2006 5:18:07 PM |
| Sample Source & type: Works | Measured by: Roderick | Analysed: Thursday, August 17, 2006 5:18:08 PM |
| Sample bulk lot ref: | Result Source: Averaged | |

| | | | |
|---|---|---|---|
| Particle Name: Insulin | Accessory Name: Hydro 2000µP (A) | Analysis model: General purpose | Sensitivity: Normal |
| Particle RI: 1.500 | Absorption: 0 | Size range: 0.020 to 2000.000 um | Obscuration: 3.96 % |
| Dispersant Name: Ethanol | Dispersant RI: 1.360 | Weighted Residual: 1.661 % | Result Emulation Off |

| | | | |
|---|---|---|---|
| Concentration: 0048 %Vol | Span: 6.758 | Uniformity: 1.94 | Result units: Volume |
| Specific Surface Area: 22.3 m²/g | Surface Weighted Mean D[3,2]: 0.180 um | Vol. Weighted Mean D[4,3]: 0.586 um | | d(0.1): 0.081 um     d(0.5): 0.235 um     d(0.9): 1.670 um

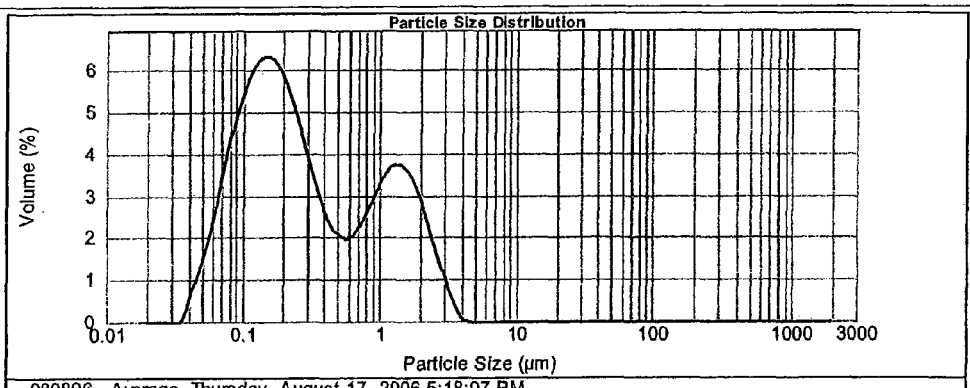

Operator notes:

Fig. 9a

 

MASTERSIZER

Parameter Report

| | | |
|---|---|---|
| Sample Name:<br>080806 - Average | SOP Name: | Measured:<br>Thursday, August 17, 2006 5:18:07 PM |
| Sample Source & type:<br>Works | Measured by:<br>Roderick | Analysed:<br>Thursday, August 17, 2006 5:18:08 PM |
| Sample bulk lot ref: | Result Source:<br>Averaged | |

| | | |
|---|---|---|
| Instrument Model:<br>Mastersizer 2000 | Displayed data channels:<br>62 | Beam length:<br>1.35 mm |
| Instrument Serial number:<br>MAL100459 | Intrument kernel version:<br>1.00 | Instrument firmware number:<br>1.05 |
| Software version:<br>5.22 | | |

| | |
|---|---|
| ccessory name:<br>Hydro 2000µP (A) | Accessory code:<br>6 |

| | | | |
|---|---|---|---|
| Particle Name:<br>Insulin | Analysis model:<br>General purpose | Sensitivity:<br>Normal | Result Emulation<br>Off |
| Particle RI:<br>1.500 | Absorption:<br>0 | Size range:<br>0.020 to 2000.000 um | Result units:<br>Volume |
| Dispersant Name:<br>Ethanol | Dispersant RI:<br>1.360 | Number of result bands:<br>70 | |

| | |
|---|---|
| Focal plane serial number:<br>2688-LOS | Characterised On:<br>Friday, October 14, 2005 12:08:36 PM |
| Side scatter serial number:<br>11711977-S | Characterised On:<br>Wednesday, March 19, 2003 1:39:31 PM |
| Large angle serial number:<br>11612665-S | Characterised On:<br>Wednesday, March 19, 2003 1:39:32 PM |
| Back scatter serial number:<br>12512210-S | Characterised On:<br>Wednesday, March 19, 2003 1:39:32 PM |
| Laser monitor serial number:<br>11911965-S | Characterised On:<br>Wednesday, March 19, 2003 1:39:33 PM |
| Blue light serial number:<br>1611950-S | Characterised On:<br>Wednesday, March 19, 2003 1:39:33 PM |

| | | | |
|---|---|---|---|
| Measurement Integration time:<br>5000 ms | Autodilution:<br>Off | Autodilution pause time:<br>0 seconds | Concentration:<br>0.0048 |
| Concentration alarm:<br>Off | Low concentration alarm triggered:<br>No | High concentration alarm triggered:<br>No | |
| Align alarm triggered:<br>No | Align alarm level:<br>50.0 | | |
| Background alarm:<br>Off | Background alarm triggered:<br>No | | |
| Result emulation filename: | Result emulation file date: | | |

Fig. 9b

Sample I.D. 080806

Compound: Bovine Insulin
Solvent: 0.1N HCl
UV Wavelength (nm): 276

Flowrate: 28.3 l/min
Duration: 10 seconds
Device: Handihaler (Boehringer Ingelheim)
Capsule: No.3 (Capsugel)

| Aerosol Performance of Sample 080806 | | | | | |
|---|---|---|---|---|---|
| | | Analysis 1 | | Analysis 2 | |
| Stage | ECD (μm) | MMAD (%) with Device | MMAD (%) without Device | MMAD (%) with Device | MMAD (%) without Device |
| Capsule + Device | Capsule Retention | 6.4 | - | 6.1 | - |
| 0 + preseparator | 9 | 11.2 | 12.0 | 14.8 | 15.8 |
| 1 | 5.8 | 4.3 | 4.6 | 3.9 | 4.1 |
| 2 | 4.7 | 4.4 | 4.7 | 3.6 | 3.8 |
| 3 | 3.3 | 5.4 | 5.7 | 5.2 | 5.6 |
| 4 | 2.1 | 5.4 | 5.8 | 7.9 | 8.4 |
| 5 | 1.1 | 4.3 | 4.6 | 5.0 | 5.3 |
| 6 | 0.7 | 9.9 | 10.6 | 4.8 | 5.1 |
| 7 | 0.4 | 7.2 | 7.7 | 5.7 | 6.1 |
| Filter | <0.4 | 41.5 | 44.3 | 43.0 | 45.8 |
| Total | | 100.0 | 100.0 | 100.0 | 100.0 |
| Loaded Dose (mg) | | 3.0 | | 1.8 | |
| Inhalable Fraction (%) | | 88 | | 84.2 | |
| Emitted Dose (%) | | 94.1 | | 94.1 | |
| Recovered Dose (%) | | 91.2 | | 97.5 | |

Before
After
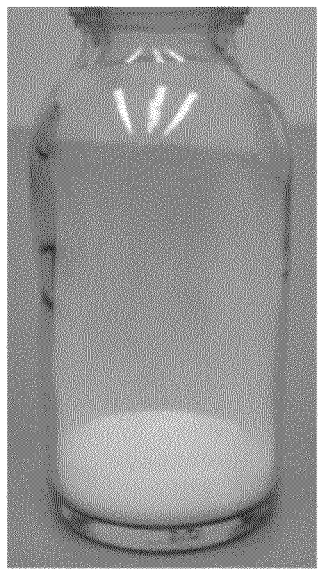
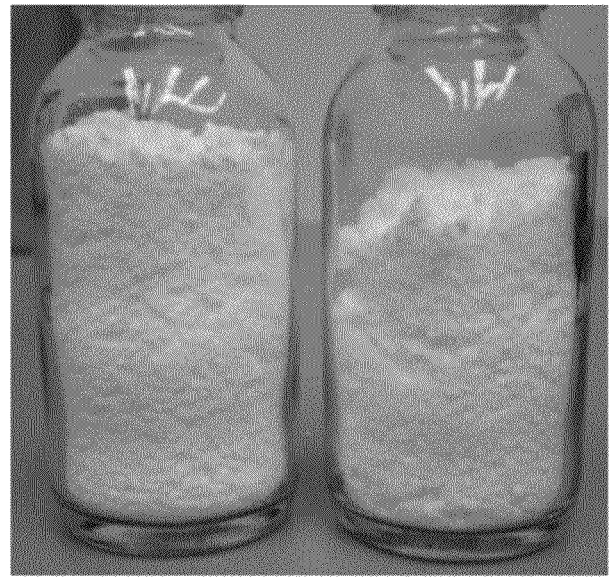
Fig. 12

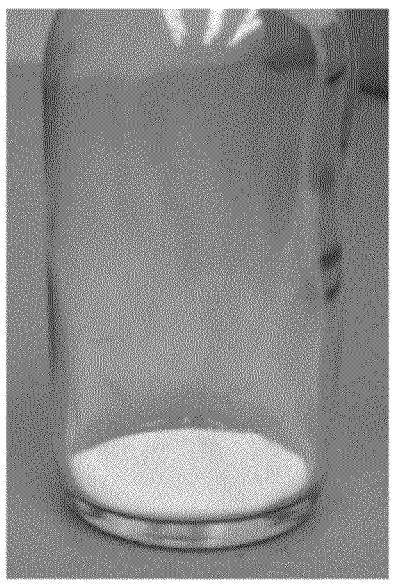 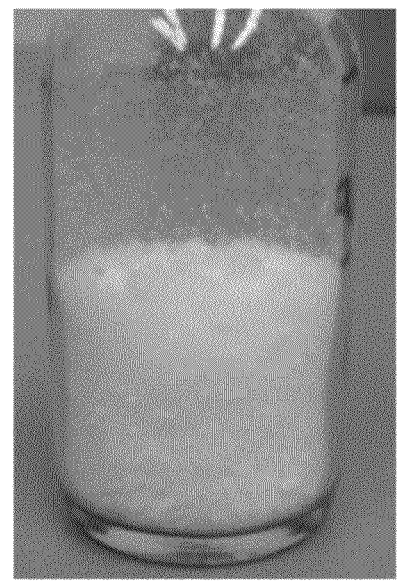
Fig. 13

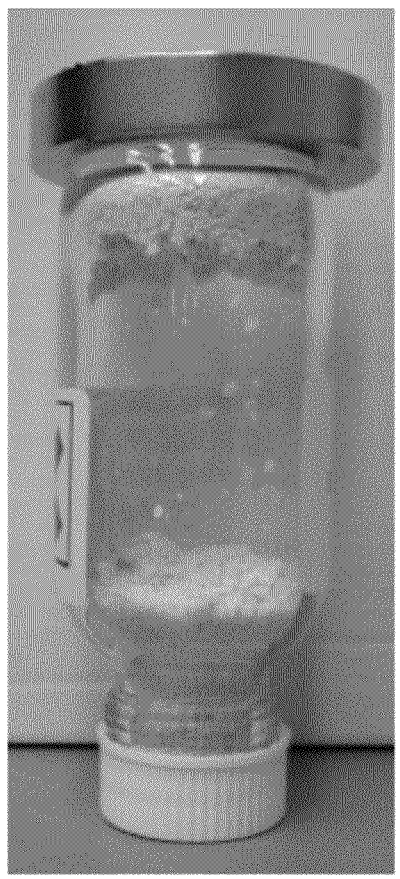
Fig. 15

PROCESS FOR PRODUCING PARTICLES VIA ATOMIZED RAPID INJECTION FOR SOLVENT EXTRACTION

This application is the National Stage of International Application No. PCT/AU2007/001515, filed Oct. 5, 2007, which claims priority to Australia Patent Application No. 2006905571, filed Oct. 6, 2006, which are incorporated by reference herein in their entirety.

TECHNICAL FIELD

The present invention relates to a method for forming small particles.

BACKGROUND OF THE INVENTION

The benefits of decreasing the particle sizes of pharmaceutical compounds are well known. Commonly referred to as micronizing, the reduction in the particle sizes of pharmaceutical compounds has brought about improvements in dissolution profiles as well as more convenient methods of delivery. The more common techniques for the micronization of pharmaceutical compounds with Dense Gas (DG) technology include the Rapid Expansion of Supercritical Solutions (RESS) process, the Gas Anti-solvent (GAS) process, the Aerosol Solvent Extraction System (ASES) process and, more recently, the Depressurization of an Expanded Liquid Organic Solvent (DELOS) process. Carbon dioxide ($CO_2$) is a commonly used DG, due in part to its vast abundance and ease of applicability. While the RESS and DELOS processes utilize dense or supercritical $CO_2$ as a solvent and/or co-solvent for pharmaceutical compound processing, the GAS and ASES processes exploit the anti-solvent effect of condensed $CO_2$ in organic solutions containing pharmaceutical compounds.

Key features of these processes are outlined below.

GAS: A volume of solution containing dissolved pharmaceutical compound(s) or working solution is introduced into a sealed vessel at atmospheric pressure. Antisolvent is then introduced into the vessel from the bottom through a sparger. The working solution is expanded and precipitation of previously dissolved compounds occurs. The precipitate is rinsed by passing carbon dioxide ($CO_2$) from the top of the vessel.

ASES: The ASES process is also known as the Supercritical Anti-solvent System (SAS). Another process that is technically similar to the ASES process is the Solution Enhanced Dispersion by Supercritical Fluids (SEDS). In ASES, working solution is physically pumped at constant flowrate into a vessel containing antisolvent through a capillary nozzle (micron size range). The flowrate of the working solution is typically in the region of 0.1 to 4 ml/min. Different nozzle configurations exist where the working solution is introduced cocurrent to antisolvent, the nozzle is energized with ultrasound etc. With SEDS, the working solution is introduced coaxially with anti-solvent to effect better mixing between the two. After delivery, e.g. spraying, of the working solution, the precipitate is rinsed with $CO_2$ to remove residual solvent.

DELOS: Working solution is introduced into a sealed vessel and is next partially expanded with $CO_2$, similar to the GAS process but without precipitation occurring. Expanded solution is then slowly depressurized over a valve into another vessel under isobaric conditions. Precipitation occurs following depressurization as a result of critical cooling of the expanded working solution as $CO_2$ flashes. The precipitate is rinsed by passing $CO_2$ or nitrogen at low pressure.

RESS: RESS is technically different to the processes described above. RESS uses supercritical fluids as the primary solvent to dissolve the pharmaceutical compound. Organic solvents are added (if any) in very small amounts to modify/increase the solubility of the pharmaceutical compound in supercritical carbon dioxide. Thus pharmaceutical compounds are loaded into a sealed vessel mounted with a frit at the exit to prevent entrainment of solid pharmaceutical compounds out of the vessel. The vessel is pressurized with supercritical fluid to operating conditions capable of dissolving the pharmaceutical compound. When necessary, organic solutions (co-solvents) may be is added to modify and increase the solubility of the pharmaceutical compound into the supercritical phase. After saturating the supercritical carbon dioxide with the pharmaceutical compound, the supercritical fluid is depressurized into another vessel through a capillary nozzle to a much lower pressure. Depressurization of the supercritical fluid causes a dramatic decrease in its solvating power and the precipitation of previously dissolved pharmaceutical compounds is effected. Precipitate is retained in the second vessel typically with a filter.

Several crystallization techniques, such as SEDS and SAS use capillary nozzles and low flowrates (0.1 to 4 ml/min) to atomize working solutions for precipitation. Such low delivery rates of working solutions make for very long and tedious processing. Existing SCF (supercritical fluid) recrystallization techniques introduce antisolvent to a working solution or vice versa gradually in eluted amounts, leading to the formation of concentration gradients. As a result, secondary nucleation and crystal growth occur at different rates depending on localized concentrations. This may lead to broad particle size distributions and inconsistent results.

Prior art processes are often difficult to scale up from laboratory scale to production scale, due to scaling factors with nozzles, flow rates etc. Exact working solution/antisolvent ratios are also often difficult, if not impossible to establish. Some of the above processes require quite complex equipment, resulting in additional equipment expense. Existing processes commonly prove difficult to scale-up because capillary nozzle spray patterns as a function of increased working solution flowrates are difficult to predict (ASES/SAS). Also, these processes require complicated design of critical equipment, for example geometrical extrapolation of nozzle design with SEDS. Capillary nozzles used in existing processes are prone to clogging and the formation of a precipitate at the nozzle tip interferes with working solution atomization. Additionally, existing processes operate with concentration gradients existing in the precipitation chamber. Scaling up equipment of these processes would alter the position and nature of these concentration gradients.

OBJECT OF THE INVENTION

It is the object of the present invention to substantially overcome or at least ameliorate one or more of the above disadvantages.

SUMMARY OF THE INVENTION

In a first aspect of the invention there is provided a process for producing particles of a substance comprising:

delivering a solution of the substance in a solvent in at least one shot into a supercritical fluid, said supercritical fluid being a non-solvent for the substance and being miscible with the solvent, and forming particles of the substance, said particles being distributed in a mixture of the solvent and the supercritical fluid.

The process may be conducted without the use of capillary nozzles or orifices to effect atomization.

The step of delivering may be conducted as a single bolus delivery of the solution. It may comprise delivering (e.g. injecting) the solution in a single shot into the supercritical fluid. It may be conducted with a flow rate of the solution into the supercritical fluid of at least about 1 L/s, or with a flow rate of between about 0.5 and about 100 L/s. The delivering may be instantaneous or nearly instantaneous or rapid. It may occur within the space of about 0.1 and 500 ms. The step of delivering the solution may be sufficiently rapid that the time for said delivering is shorter than the time for formation of the particles. The rate of delivering may be sufficiently rapid that droplets of the solution are distributed throughout the supercritical fluid before formation of the particles. The rate of delivering may be sufficiently energised that droplets of the solution are distributed throughout the supercritical fluid before formation of the particles. It may be sufficiently rapid and/or energized that the solution is distributed throughout the supercritical fluid following said delivering. It may be sufficiently rapid and/or energized that droplets of the solution are distributed substantially homogeneously or homogeneously throughout the supercritical fluid following said delivering.

If more than one shot is used, the shots may be into the same or different precipitation chambers. If more than one single shot is used, and if the shots are into the same precipitation chamber, they should be substantially simultaneous or simultaneously. If the shots are into different precipitation chambers, they may or may not be simultaneous.

In this context, the term substantially simultaneous may refer to events that are sufficiently closely spaced that the particle size of the particles formed by the process is the same as, or smaller than, that obtained from a single shot. The shots may be separated by less than about 500 ms, or less than about 100 or 10 ms, or between about 0 and about 500 ms, between about 0 and about 100 ms or between about 0 and 10 ms.

In the step of delivering, the ratio of the amounts of the solvent and the supercritical fluid may be such that the substance has low solubility in a mixture of the solvent and the supercritical fluid in said ratio. The ratio may be for example less than about 1:10 on a volume basis, a weight basis or a mole basis. This ratio may relate to the amount of solvent in a single shot, or to the total amount of solvent in the shots in said step of delivering. During and immediately after the step of forming the particles, the conditions (temperature and pressure) in the precipitation chamber should be such that the mixture of supercritical fluid and solvent is in its supercritical state. Commonly during this step the temperature of the mixture will be about the same (e.g. within about 5 Celsius degrees) as that of the supercritical fluid prior to the step of delivering, and the pressure of the mixture will be slightly higher (e.g. about 1 to 20 bar higher) than that of the supercritical fluid prior to the step of delivering.

The process may additionally comprise the step of pressurising the solution with a gas to a pressure greater than that of the supercritical fluid before delivering the solution into the supercritical fluid, said gas having low solubility in the solution, or being substantially insoluble in the solution.

The process may additionally comprise pressurising the solution to a pressure at least about 20 bar greater than the pressure of the supercritical fluid before delivering the solution into the supercritical fluid.

The step of delivering may comprise opening an injection valve so as to permit the solution to combine with the supercritical fluid. The injection valve may be for example a ball valve, or some other valve that is capable of being opened rapidly.

The step of forming may consist of forming the particles throughout the mixture of the solvent and the supercritical fluid. The step of forming may consist of forming the particles homogeneously, or substantially homogeneously, throughout the mixture of the solvent and the supercritical fluid.

The process may additionally comprise separating the particles from the mixture of the solvent and the supercritical fluid. The step of separating may be conducted while maintaining the mixture in its supercritical state. The process may additionally comprise washing the particles with the supercritical fluid.

The process may additionally comprise depressurising the particles to ambient pressure after said separating.

The supercritical fluid may comprise supercritical carbon dioxide. The solvent may be a polar solvent. It may be a non-aqueous solvent or an aqueous solvent. The substance may be, or may comprise, a pharmaceutically active substance. The substance may be therapeutically active. The substance may be for example insulin, hydroxypropylated beta cyclodextrin, Budesonide or EUDRAGIT™S100 (poly-(methacrylic acid-co-methyl methacrylate) 1:2) or any combination thereof. The insulin may be a natural insulin, synthetic insulin, an insulin analogue, an insulin derivative or any combination thereof. The substance may be a carrier or it may be a pharmaceutically or veterinarily acceptable carrier in combination with a pharmaceutically or veterinarily active substance. The substance may be a peptide, a protein or analogue thereof, a nucleic acid, an organic chemical or an antibiotic (e.g. gentamycin). The substance may be, or may comprise, a dry powder vaccine, a bronchodilator, human growth hormone, human growth hormone analogue, human growth hormone derivative, heparin, erythropoietin, epoietin, Factor VIII, G-CSF, Interferon Alpha, Interferon Beta, Interferon Gamma, Interleukin-2, Actimmune (If γ), Activase (TPA), BeneFix (F IX), Betaseron (If β), Humulin, Novolin, Lispro, Insulin Aspart, Glargine, Pegademase (AD), Epogen, Regranex (PDGF), Novoseven (F VIIa), Intron-A, Neupogen, Pulmozyme, Infergen, an antibody, a monoclonal antibody, an enzyme or a carbohydrate, or Generally Regarded As Safe (GRAS) excipients, polyethylene glycol (PEG) or polyethylene oxide (PEO), a polyethylene glycol oligomer, a polyethylene oxide oligomer or any combination thereof, for example, or may comprise a combination of any one or more of the above with a pharmaceutically or veterinarily acceptable carrier.

The solution may comprise suspended particles. In this case, the process may be a process for at least partially coating the suspended particles with the substance. It may be a process for producing particles each of which comprises a core particle at least partially coated with the substance. Thus the solution may comprise core particles, whereby the particles of the substance produced by the process comprise the core particles at least partially coated with the substance.

The process may additionally comprise the steps of:

delivering a solution of a second substance in a second solvent in at least one shot into the supercritical fluid, said supercritical fluid being a non-solvent for the second substance and being miscible with the second solvent, and forming at least partially coated particles comprising the particles of the substance at least partially coated by the second substance, said at least partially coated particles being distributed in a mixture of the solvent, the second solvent and the supercritical fluid.

Any one or more of the above options may, where appropriate, be combined in a particular embodiment of the invention.

In an embodiment of the invention there is provided a process for producing is particles of a substance comprising:

delivering a solution of the substance in a solvent in a single shot into a supercritical fluid, said supercritical fluid being a non-solvent for the substance and being miscible with the solvent, and forming particles of the substance, said particles being distributed in a mixture of the solvent and the supercritical fluid.

In another embodiment of the invention there is provided a process for producing particles of a substance comprising:

pressurising a solution of the substance in a polar solvent with a gas, said gas having low, optionally negligible, solubility in the solution;

delivering the solution in a single shot into a supercritical fluid, said supercritical fluid being a non-solvent for the substance and being miscible with the solvent and said supercritical fluid being at a pressure of at least about 20 bar less than that of the solution after the step of pressurising and before the step of delivering, forming particles of the substance, said particles being distributed in a mixture of the solvent and the supercritical fluid, separating the particles from the mixture of the solvent and the supercritical fluid while maintaining the mixture in its supercritical state, and washing the particles with the supercritical fluid;

wherein the ratio of the amounts of the solvent and the supercritical fluid is such that the substance has low solubility in a mixture of the solvent and the supercritical fluid in said ratio.

In another embodiment of the invention there is provided a process for producing particles of a substance comprising:

pressurising a solution of the substance in a polar solvent with nitrogen to between about 140 and about 200 bar;

delivering the solution within a time period of between about 1 and about 500 ms, or between about 1 and 100 ms, into supercritical carbon dioxide, said supercritical carbon dioxide being at a pressure in the range of about 20 bar to about 100 bar less than that of the solution after the step of pressurising and before the step of delivering, forming particles of the substance, said particles being distributed in a mixture of the solvent and the supercritical fluid, separating the particles from the mixture of the solvent and the supercritical carbon dioxide while maintaining the mixture in its supercritical state, and washing the particles with the supercritical fluid;

wherein the ratio (volume:volume, mole:mole or weight:weight) of the amounts of the solvent and supercritical carbon dioxide is between about 1:10 and about 1:50.

In another embodiment of the invention there is provided a process for producing particles of a substance comprising:

pressurising a solution of the substance in a polar solvent with nitrogen to between about 140 and about 200 bar;

delivering the solution into supercritical carbon dioxide, said supercritical carbon dioxide being at a pressure in the range of about 20 bar to about 100 bar less than that of the solution after the step of pressurising and before the step of delivering, forming particles of the substance, said particles being distributed in a mixture of the solvent and the supercritical fluid, separating the particles from the mixture of the solvent and the supercritical carbon dioxide while maintaining the mixture in its supercritical state, and washing the particles with the supercritical fluid;

wherein the ratio (volume:volume, mole:mole or weight:weight) of the amounts of the solvent and supercritical carbon dioxide is between about 1:10 and about 1:50 and wherein the delivering is at a rate sufficient that the particles are formed with a mean particle diameter of between about 10 about 200 nm or between about 10 and 100 nm, and/or with a bulk density of greater than about 1 and 50 mg/ml, and/or with a specific surface area of greater than about 10 $m^2/g$.

The rate may be between about 0.01 and 100 L/s, or between about 1 and 100 L/s or between about 10 and 100 L/s.

In another embodiment there is provided a process for producing encapsulated particles of a substance comprising:

a) delivering a first solution, comprising the substance dissolved in a first solvent, in a single shot into a supercritical fluid, said supercritical fluid being a non-solvent for the substance and being miscible with the first solvent, b) forming particles of the substance, said particles being distributed in a mixture of the solvent and the supercritical fluid, c) delivering a second solution, comprising an encapsulant dissolved in a second solvent, in a single shot into the supercritical fluid having the particles distributed therethrough, said supercritical fluid being a non-solvent for the encapsulant and being miscible with the second solvent, and d) forming a coating of the encapsulant on at least some of the particles of the substance.

Step c) should be conducted after step a), preferably after step b). The encapsulant may be a protective material in order to protect the substance from an environment in which the encapsulated particles are placed, or it may be a taste-masking material in order to mask the taste of the substance during oral ingestion of the encapsulated particles. The encapsulant may be biocompatible and/or biodegradable in the human body. During the delayed degradation of encapsulant in-vivo, sustained or delayed release of coated material into the body may be achieved. The encapsulant may comprise one or more types of lipid, polyethylene glycol or other Generally Regarded As Safe excipients or a combination of any two or all or these. The first solvent may be the same as the second solvent or it may be different. It will be understood that using a modification of this embodiment, additional layers may also be formed on the particles by repeating steps c) and d) one or more times (e.g. 1, 2, 3, 4 or more than 4 times). If these steps are repeated, the solvent and the encapsulant at each repetition may be the same as or different to the solvent and the encapsulant respectively of another repetition. The present invention provides layered particles when made by the process described herein. The particles may have 1, 2, 3, 4, 5 or more than 5 layers. Each time step c) is conducted the amount and nature of the solvent should be such that the mixture of supercritical fluid and solvents is a single phase, preferably a single supercritical phase, and is a non-solvent for the particles and the encapsulated particles. Therefore each coating formed at step d) may be a complete coating on the particles or may be a partial (e.g. at least about 50, 60, 70, 80, 90 or 95% coating) on the particles.

Solid particles to be coated may be prepared as a suspension in a solvent, wherein the solvent contains a dissolved encapsulant. This suspension may then be delivered into the supercritical fluid. After said delivery, the encapsulant may form a coating on at least some of the solid particles. Solid particles suitable for such a coating technique include, but are not limited to, magnetic iron oxide particles, solid pharmaceutical ingredients and their derivatives, implantable microcapsules and biodevices, therapeutic agents such as erythropoietin, epoietin, human stem cells, nucleotides and other cofactors, agents used for in-vivo imaging and biological agents requiring protection from environmental damage.

Thus in another embodiment there is provided a process for producing particles, said particles comprising core particles at least partially encapsulated by an encapsulant, said process comprising:
 delivering a dispersion of the core particles in a solvent, said dispersion comprising the encapsulant in solution, in at least one shot into a supercritical fluid, said supercritical fluid being a non-solvent for the core particles and for the encapsulant and being miscible with the solvent, and
 forming the particles, said particles being distributed in a mixture of the solvent and the supercritical fluid.

In another embodiment of the invention the substance comprises more than one compound, for example 2, 3, 4, 5 or more than 5 compounds. These may all be in solution in the solvent during the step of delivering the solution into the supercritical fluid, or one or more of them may be in suspension or otherwise dispersed in the solvent. Compounds that are not in solution should be sufficiently finely divided and in sufficiently low concentration in the solvent that they do not substantially impede the delivery of the solution into the supercritical fluid. In this embodiment, the more than one compound may be coprecipitated in the supercritical fluid. The process may form particles each of which, or the majority of which, comprise each of said compounds. In an example, one of the compounds may be a carrier for one or more active substances (e.g. pharmaceutically or veterinarily active substances). In another example the compounds comprise two or more pharmaceutical compounds which act synergistically.

There is also provided a process for producing particles of a substance comprising:
 delivering a solution of the substance in a solvent in more than one single shot into a supercritical fluid, said supercritical fluid being a non-solvent for the substance and being miscible with the solvent, and
 forming particles of the substance, said particles being distributed in a mixture of the solvent and the supercritical fluid.

The supercritical fluid may be located in one or more precipitation chambers. The shots may be into the same or different precipitation chambers. If the shots are into the same precipitation chamber, they should be delivered simultaneously or substantially simultaneously (e.g. within about 0 and about 500 ms). In this case, it may be preferable to use a precipitation that is sufficiently large, and have delivery points for delivering the solution to the supercritical fluid in the precipitation chamber sufficiently spaced, so that is the particle size of the particles formed by the process is the same as, or smaller than, that obtained from a single shot. If the shots are into different precipitation chambers, they may or may not be simultaneous.

In a second aspect of the invention there is provided an apparatus for producing particles of a substance, said apparatus comprising:
 a pressurisable injection chamber capable of receiving a solution of the substance in a solvent;
 a precipitation chamber capable of maintaining supercritical conditions for a supercritical fluid, said supercritical fluid being a non-solvent for the substance and being miscible with the solvent, said precipitation chamber being fitted with an inlet port for admitting the supercritical fluid thereto;
 a conduit connecting the injection chamber and the precipitation chamber, said conduit comprising an injection valve disposed such that when the injection valve is in an open condition the injection chamber communicates with the precipitation chamber and when the injection valve is in a closed condition the injection chamber is isolated from the precipitation chamber; and
 an outlet port communicating with the precipitation chamber for allowing a mixture of the supercritical fluid and the solvent to exit the precipitation chamber.

In use, the injection chamber should be pressurised to a pressure greater than the pressure in the precipitation chamber. The pressure difference between the injection chamber and the precipitation chamber may be of a magnitude so as to cause rapid delivery of a shot of the solution of the substance in the injection chamber into the precipitation chamber when the injection valve is in an open condition.

The apparatus may have no capillary nozzles or orifices to effect atomization. The apparatus may additionally comprise a separation device for separating the particles from the mixture of the solvent and the supercritical fluid while maintaining the mixture in its supercritical state. The separation device may comprise a filter, e.g. a frit. It may be located at an outlet from the precipitation chamber, or may be located in line separate from the precipitation chamber.

The apparatus may comprise a pressuriser for pressurising the injection chamber. The pressuriser may be capable of pressurising the injection chamber to a pressure greater than the pressure required to maintain supercritical conditions for the supercritical fluid.

The conduit may extend into the precipitation chamber. The minimum internal diameter of the conduit may be sufficiently large to allow single shot delivery of the solution into the supercritical fluid. It may be sufficiently large to allow single shot, e.g. rapid, instantaneous or near instantaneous, delivery of the solution into the supercritical fluid. The conduit may terminate in a nozzle, said nozzle being located within the precipitation chamber. The nozzle may be a non-capillary nozzle. It may have sufficiently large diameter that delivery of the solution through the nozzle can occur without choked flow. The conduit may be such that it does not comprise a capillary nozzle or orifice.

The volume of the precipitation chamber may be at least about 10 times the volume of the injection chamber.

Any one or more of the above options may, where appropriate, be combined in a particular embodiment of the invention.

In a third aspect of the invention there is provided a particulate substance, the particles of said particulate substance being made by a process comprising:
 delivering a solution of the substance in a solvent in a single shot into a supercritical fluid, said supercritical fluid being a non-solvent for the substance and being miscible with the solvent, and forming particles of the substance, said particles being distributed in a mixture of the solvent and the supercritical fluid.

The ratio of the amounts of the solvent and the supercritical fluid should be such that the substance has low solubility in a mixture of the solvent and the supercritical fluid in said ratio.

The particulate substance may be made by the process of the first aspect of the invention, optionally with any one or more of the optional features thereof described above.

The particles of the particulate substance may have a mean particle size of less than about 100 nm. The particulate substance may have a specific surface area of at least about 10 $m^2/g$ or at least about 20 $m^2/g$, and may be in the range of about 10 $m^2/g$ to about 100 $m^2/g$. The particles may be aggregated into loosely bound aggregates. The loose aggregates may have a mean diameter of less than about 20 microns in mean diameter, or between about 1 and about 20 microns.

In a fourth aspect of the invention there is provided a particulate substance having a mean particle size of between about 10 and about 200 nm, said particulate substance is comprising a drug for pulmonary delivery. The particulate substance may have a bulk density between about 1 and about 50 mg/ml or between about 5 and about 20 mg/ml. The particulate substance may have a specific surface area of greater than about 10 $m^2/g$, or between about 10 and about 100 $m^2/g$. It may be in the form of loose aggregates having a mean diameter of less than about 20 microns, or between about 1 and about 20 microns.

In a fifth aspect of the invention there is provided a method for treating a condition in a patient, said method comprising administering a particulate substance according to the third or fourth aspect of the invention to the patient, said substance being indicated for treatment of the condition. The administration may be pulmonary administration. It may be by inhalation. It may be by nasal inhalation or by oral inhalation. The particulate substance may be administered in a therapeutically or veterinarily effective amount. The administration may be self-administration.

In a sixth aspect of the invention there is provided a particulate substance wherein the bulk density of the particulate substance is sufficiently low that its aerodynamic properties are more dependent on its bulk density than on particulate size (i.e. than on the size of particles of the particulate substance). This may be evidenced by the different particle size distributions obtained from laser diffraction and cascade impaction. The bulk density of the particulate substance may be sufficiently low that its aerodynamic properties are less dependent on the mean geometric particle diameter of the particles of the particulate substance than on the bulk density of the particulate substance. The particulate substance may have a mean geometric particle size of between about 10 and about 200 nm. The particulate substance may comprise a drug for pulmonary delivery. The particulate substance may have a bulk density between about 1 and about 50 mg/ml or between about 5 and about 20 mg/ml. The particulate substance may have a specific surface area of greater than about 10 $m^2/g$, or between about 10 and about 100 $m^2/g$. It may be in the form of loose aggregates having a mean diameter of less than about 20 microns, or between about 1 and about 20 microns. The particulate substance may be engineered to a bulk density that enables site specific deposition of the particulate substance in the lungs of a patient using a simple inhaler device. The particulate substance may be made by the process of the present invention. There is also provided an inhaler device loaded with a drug for pulmonary delivery, said drug being in the form of a particulate substance as described in the third, fourth or sixth aspect of the invention.

The process of the present invention may be used to generate a particulate substance with properties (e.g. bulk density, mean particle size, particle size distribution) that enable is the particulate substance to be delivered following inhalation thereof specifically to laryngeal, tracheal, bronchial or peripheral deposition, or any combination thereof. This may be useful for therapeutic treatment of either localized disorders such as laryngeal damage and vocal cord rehabilitation, Chronic Obstructive Pulmonary Disease (COPD) management, allograft anti-rejection, or for treatment of disorders via introducing pharmaceutical agents into the systemic circulation.

There is also provided the use of a particulate substance according to the third, fourth or sixth aspect of the invention for the manufacture of a medicament for the treatment of a condition for which the substance is indicated.

BRIEF DESCRIPTION OF THE DRAWINGS

A preferred embodiment of the present invention will now be described, by way of an example only, with reference to the accompanying drawings wherein:

FIG. 7 shows photographs of insulin (left) and of insulin particles prepared by the present invention (right);

FIG. 9 shows a particle size analysis report of insulin particles produced by the process of the present invention;

FIG. 10 shows numerical results of in-vitro inhalability testing of insulin particles produced by the process of the present invention;

FIG. 12 shows photographs of hydroxypropylated beta-cyclodextrin (HP βCD) before and after formation into particles by the process of the present invention;

FIG. 13 shows photographs of EUDRAGIT™S100 (poly-(methacrylic acid-co-methyl methacrylate) 1:2) before and after formation into particles by the process of the present invention;

FIG. 15 shows photographs of the encapsulated iron particles of FIG. 14 a magnet applied to the top of the bottle to illustrate the magnetic properties of the particles.

DETAILED DESCRIPTION OF THE PREFERRED EMBODIMENTS

Figure 1:
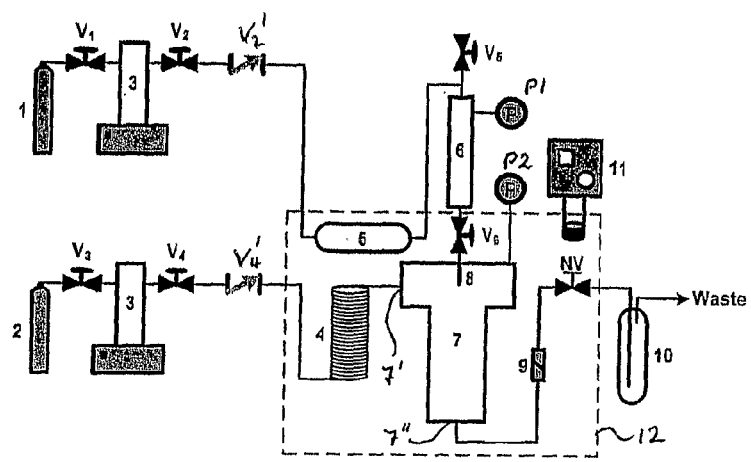
FIG. 1 is a diagrammatic representation of an apparatus for conducting the process of the present invention.
Figure 2:
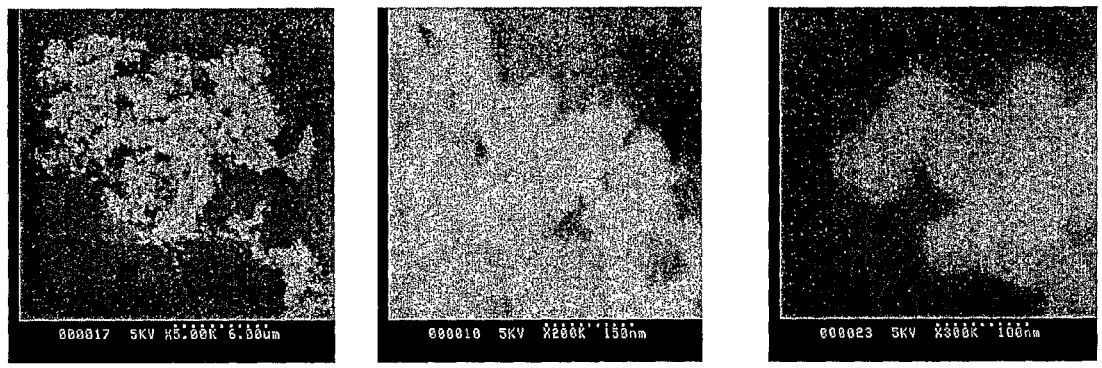
FIG. 2 shows SEM (scanning electron microscope) photographs of insulin particles produced using the process of the present invention.
Figure 3:
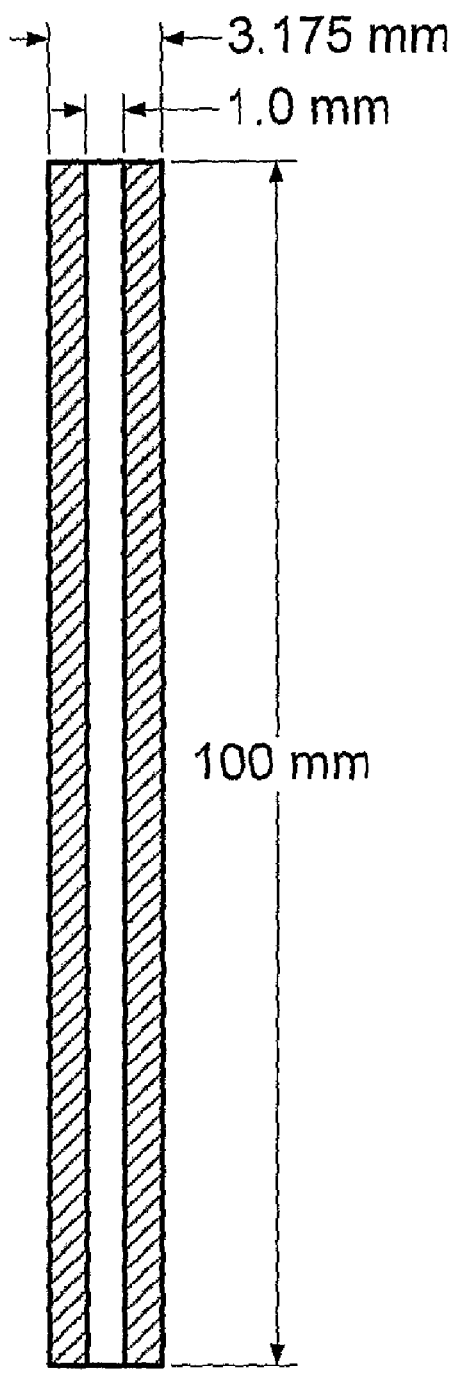
FIG. 3 Schematic of 1.0 mm I.D. Nozzle.
Figure 4:
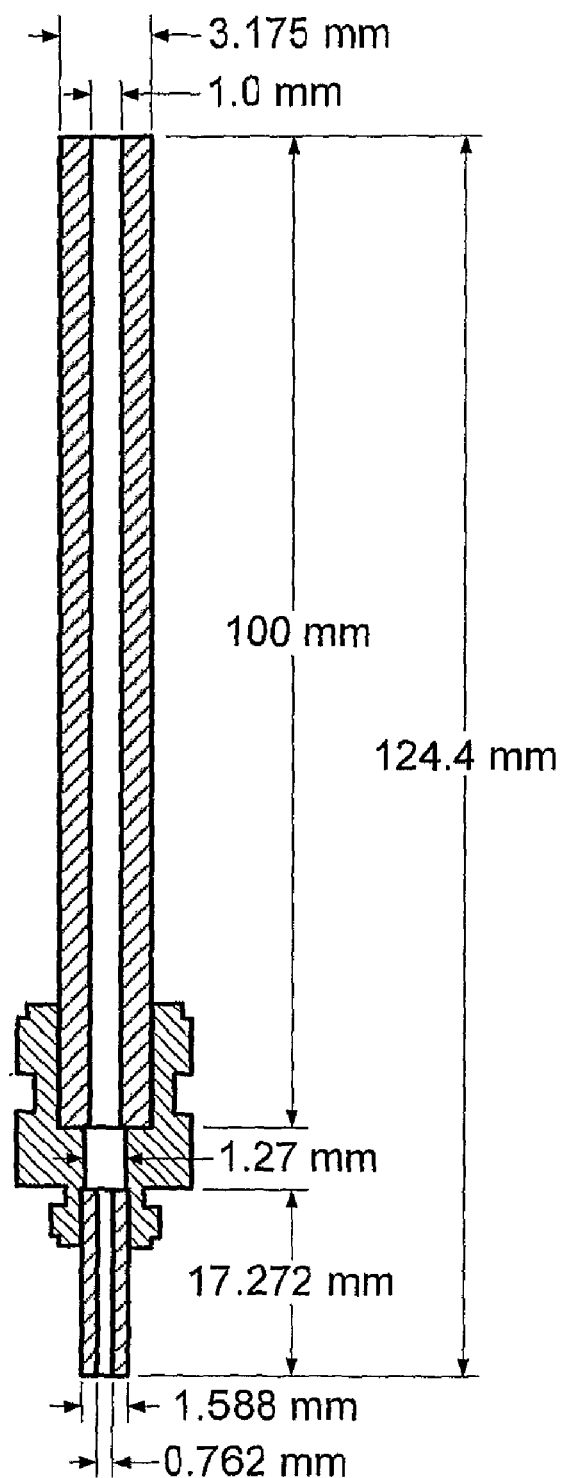
FIG. 4 Schematic of 0.762 mm I.D. Nozzle
Figure 5:
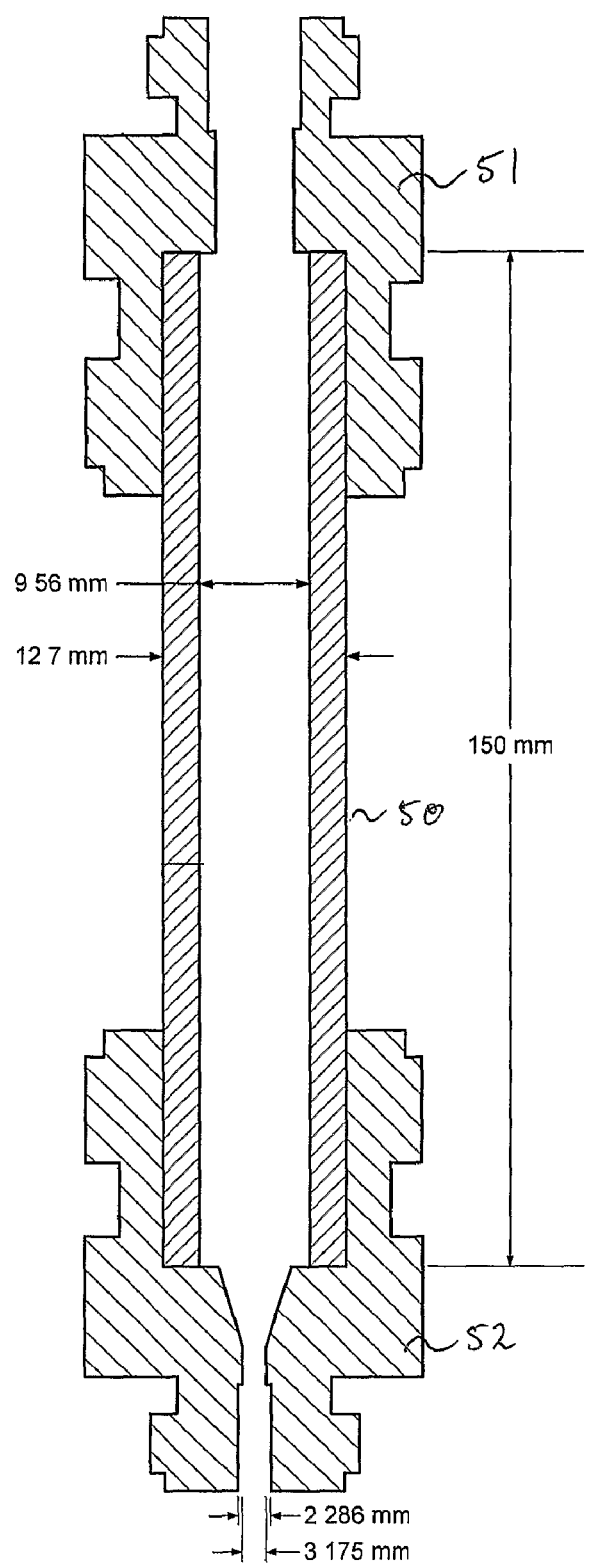
FIG. 5 shows a schematic diagram of the injection chamber used in the example.
Figure 6:
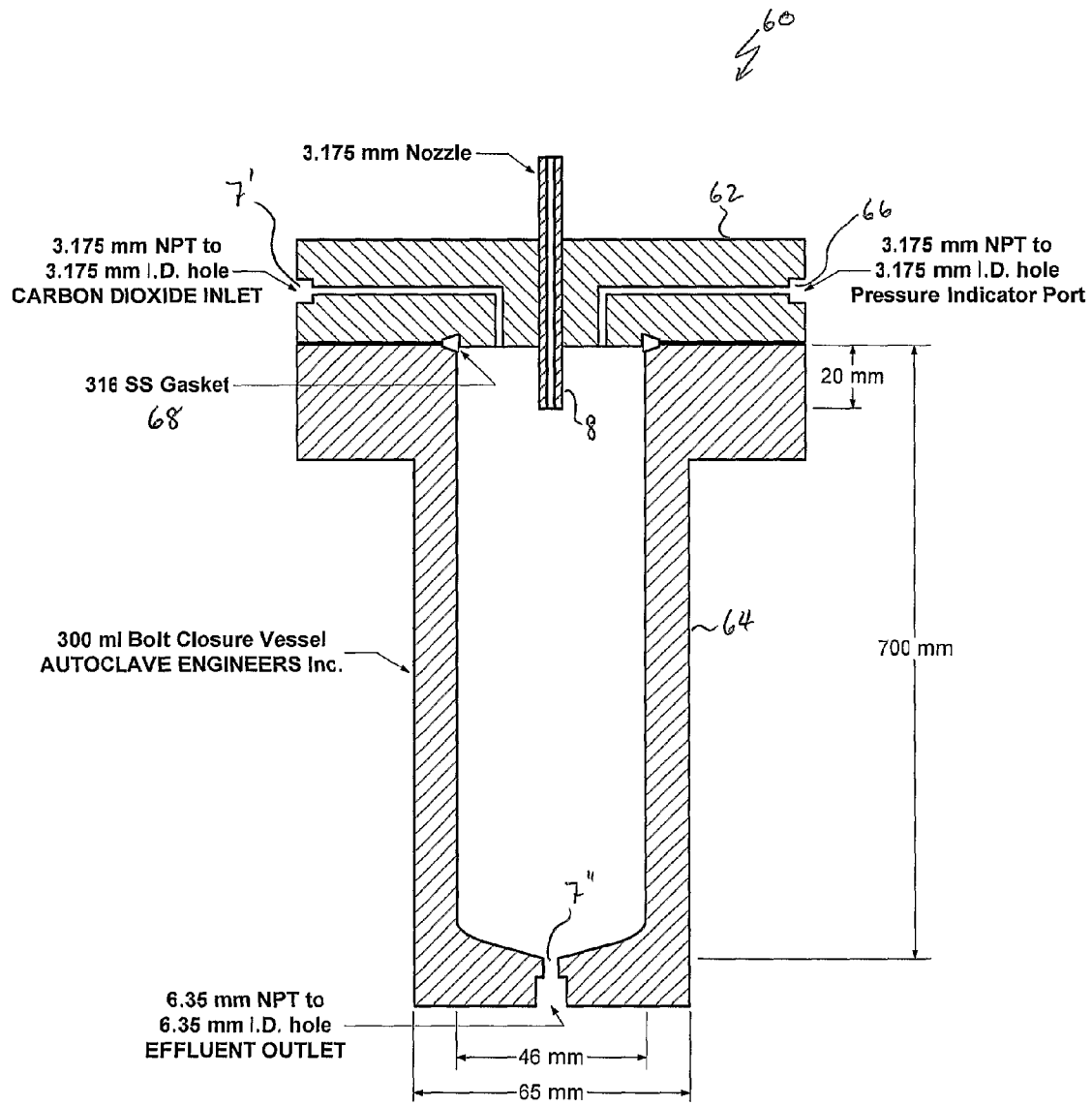
FIG. 6 shows a schematic diagram of the precipitation chamber used in the example.
Figure 8:
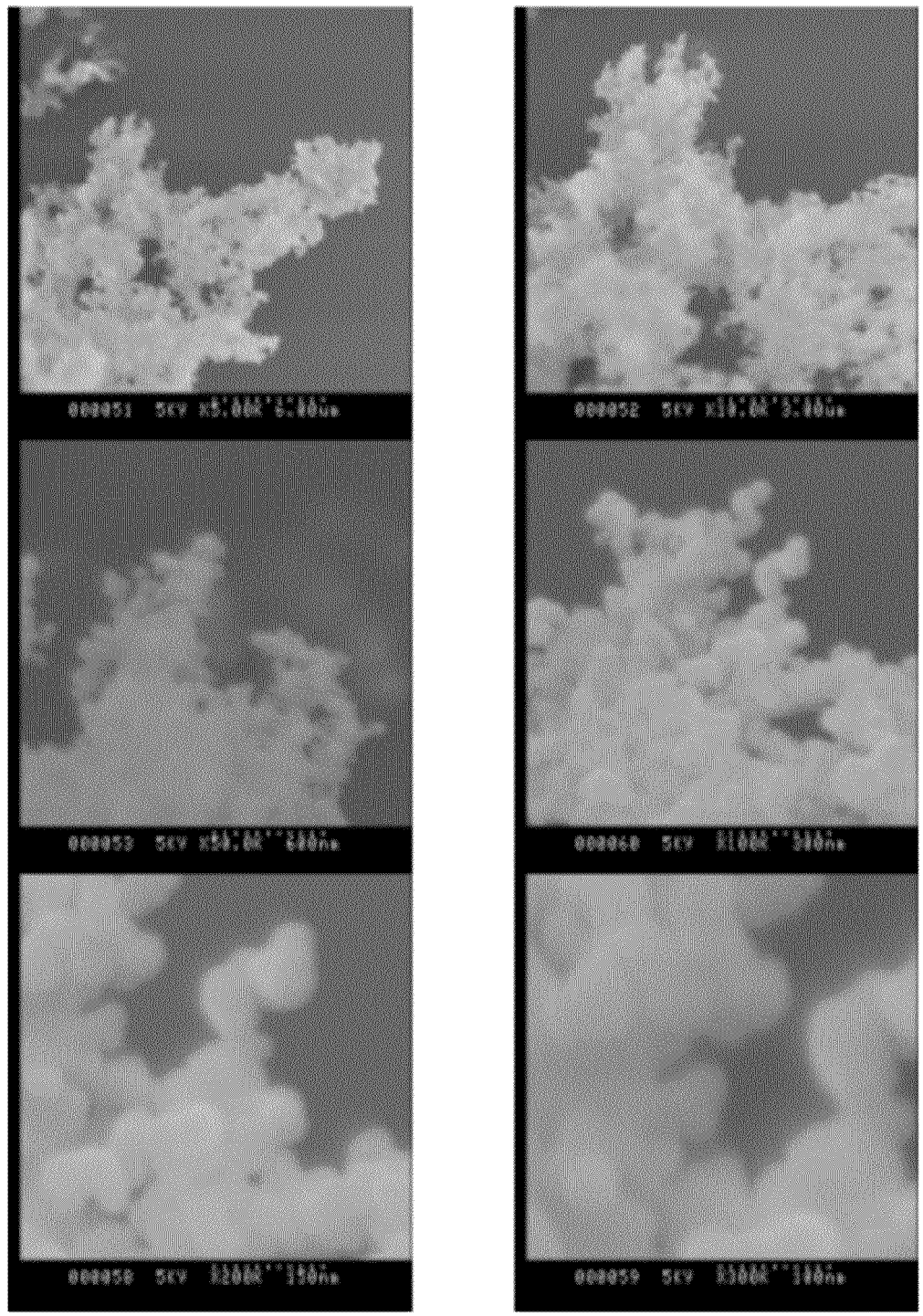
FIG. 8 shows electron micrographs of particulate substances produced by the process of the present invention.

The present invention relates to a method for forming small particles of extremely low bulk density and enhanced aerodynamic performance. The process of the invention may be used to produce particles of a single substance, or particles comprising a homogeneous mixture of two or more substances. The method may also be used to process suspensions and perform coating applications. The absence of capillary nozzles in the present process enables the injection of suspensions into the precipitation chamber, and subsequent formation of coated particles. Prior art processes have had difficulty in achieving this, as the use of capillary nozzles can lead to clogging of the nozzle with particles in the suspension.

The present invention relates to a process for producing particles of a substance comprising delivering a solution of the substance in a solvent (i.e. a working solution) in a single shot into a supercritical fluid. The delivery may take the form of a single bolus injection. The delivery may be such that the entire volume of the working solution is delivered into the supercritical fluid within a very short time, or at about the same time, or in a single bolus. The supercritical fluid is a non-solvent for the substance and is miscible with the solvent. Following the delivering, particles of the substance are formed, said particles being distributed in a mixture of the solvent and the supercritical fluid. This process is referred to as ARISE (Atomised Rapid Injection for Solvent Extraction).

It is thought that since, in the present invention, the entire volume of working solution is introduced into antisolvent (supercritical fluid) at about the same time in order to achieve a homogeneous mixture of working solution with antisolvent, the bulk of precipitate should experience similar rates of formation, leading to a more homogeneous product than is obtained using prior art processes. In the context of the present invention, the terms "antisolvent" and "non-solvent" may be considered interchangeable. Since excess volume is made available for recrystallization to occur, nucleation density may be lowered, leading to precipitate formation occurring over a large spatial volume. The low nucleation density may allow the formation of product with lower bulk densities than those previously obtained. The present invention is preferably operated such that atomization is not a function of nozzle (conduit) aperture, or at least the effect of nozzle aperture on atomisation is minor relative to other factors. This may be achieved by using nozzle sizes in a range in which the nozzle size is not a controlling factor for the rate of delivery of the working fluid into the supercritical fluid. This enables the simplification of the design of the equipment, and obviates the use of capillary nozzles. The injection may occur through a single nozzle (conduit) or through multiple nozzles (conduits), each of which conforms to the above description.

If more than one single shot is used, and if the shots are into the same precipitation chamber, they should be substantially simultaneous or simultaneously. They may occur sufficiently close together that no shot is made following particle formation from solution delivered in a preceding shot. The shots may occur within a time period of less than about 500 ms, or less than about 400, 300, 200, 100, 50, 20 or 10 ms, or between about 5 and about 500 ms, or between about 10 and 500, 20 and 500, 50 and 500, 100 and 500, 200 and 500, 5 and 200, 5 and 100, 5 and 50, 5 and 20, 20 and 50, 50 and 100, 100 and 200, 200 and 300, 300 and 400, 10 and 100, 10 and 50 or 20 and 50 ms, e.g. about 5, 10, 15, 20, 25, 30, 35, 40, 45, 50, 60, 70, 80, 90, 100, 150, 200, 250, 300, 350, 400, 450 or 500 ms.

The rate of delivering of the, or each, shot may be sufficiently rapid that droplets of the solution are distributed throughout the supercritical fluid before formation of the particles. The rate of delivering of the, or each, shot may be sufficiently energised that droplets of the solution are distributed throughout the supercritical fluid before formation of the particles. The rate of delivering of the, or each, shot may be sufficiently rapid and/or energized that the solution is distributed throughout the supercritical fluid following said delivering. The rate of delivering of the, or each, shot may be sufficiently rapid and/or energized that droplets of the solution are distributed substantially homogeneously or homogeneously throughout the supercritical fluid following said delivering. If more than one shot is delivered, the shots may be delivered from the same injection chamber or different injection chambers. They may be made through the same conduit or different conduits. They may enter the precipitation chamber(s) through the same nozzle or through different nozzles. The apparatus for producing the particles may comprise a controller for controlling the timing of the delivery of the solution. The controller may be a programmable controller and should be coupled electronically with one or more of the valves of the apparatus which control delivery of the solution to the precipitation chamber(s). The controller may also control other valves in the apparatus, e.g. those through which supercritical fluid, optionally together with the particles, exits the is precipitation chamber.

The present invention aims to minimise the occurrence of concentration gradients in precipitation chamber by using an oversized precipitation chamber. Oversizing the precipitation chamber also allows for increasing process throughput simply by increasing the volume of working solution introduced. This may additionally be achieved without operating too near to the limit of non-ideality (i.e. the point at which the saturation level of the working solution in antisolvent is exceeded).

In one aspect, the present invention provides a method for preparing a substance in particulate form, comprising introducing a solution of the substance in a solvent into a precipitation chamber containing an anti-solvent supercritical fluid, and allowing the supercritical fluid to extract the solvent from the solution to form particles of the substance. The pressure and temperature in the precipitation chamber should be above the critical pressure and critical temperature respectively of the supercritical fluid. The solution should be introduced in a single shot, or in more than one shot, or in a single bolus delivery or in more than one bolus delivery.

A shot, as used herein, may refer to delivery of the solution in a single bolus delivery or to the delivery of the solution in 2, 3, 4, 5, 6, 7, 8, 9, 10, 11, 12 or more shots or bolus deliveries into a single volume. The single volume may be between 3 and 100 times the volume of a single shot. Thus delivery of a shot of the solution may deliver the solution sufficiently rapidly that the entire shot is delivered prior to formation of particles from droplets of the solution. A single shot may comprise between about 0.2 and about 20 $cm^3$ volume, or between about 0.2 and 10, 0.2 and 5, 0.2 and 2, 0.2 and 1, 0.5 and 20, 0.5 and 10, 0.5 and 5, 1 and 20, 50 and 20, 10 and 20, 1 and 5, 5 and 10, 5 and 20, 10 and 20, 5 and 15 or 8 and 12 $cm^3$, e.g. about 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19 or 20 $cm^3$. Where there is more than one bolus delivery, the volume of each shot or bolus delivery may be between about [(0.2 and about 20 $cm^3$)/total number of shots], into a single volume.

The delivering should preferably be sufficiently rapid that the solution is delivered, e.g. sprayed, into the supercritical fluid, and droplets of the solution are dispersed therethrough before formation of the particles. Thus particle formation preferably occurs throughout the precipitation chamber and as such, throughout the supercritical fluid. It is thought that this occurs by a process in which the solvent of the solution is diluted by the supercritical fluid to the extent that the combination is a poor solvent for the particles.

The delivering may be under conditions in the precipitation chamber that avoid or is minimise agglomeration of droplets in the precipitation chamber. It may be under conditions (pressures, rate) that promote nucleation within droplets of the fluid in the precipitation chamber. The delivery may be under conditions in the precipitation chamber whereby the particles are not formed from aggregated droplets. The solution prior to delivery from the injection chamber to the precipitation chamber may have no particles therein. Alternatively it may have particles therein, provided the particles are suspended in the solvent and are sufficiently small diameter and in sufficiently low concentration that they do not clog or partially clog the conduit or nozzle. The delivering should be such that at least some of the substance precipitates, i.e. is formed into particles. It may be such that at least about 80, 85, 90, 95, 96, 97, 98, 99 or 100% of the substance precipitates, or between about 80 and 100, 80 and 99, 80 and 98, 80 and 97, 80 and 96, 80 and 95, 80 and 90, 85 and 100, 90 and 100, 95 and 100, 96 and 100, 97 and 100, 98 and 100 or 99 and 100%. The delivering may be such as to form a particulate substance having a bimodal distribution when measured using a laser light scattering apparatus. The bimodal distribution may be such that the smaller of the two modes has a peak at about 10 and 200 nm, or between about 20 and 200, 50 and 200, 100 and 200, 10 and 150, 10 and 100, 10 and 50, 10 and 40, 20 and 100, 20 and 50 or 20 and 40 nm, e.g. about 10, 15, 20, 25, 30, 35, 40, 45, 50, 60, 70, 80, 90, 100, 110, 120, 130, 140, 150, 160, 170, 180, 190 or 200 nm and the larger of the two modes has a peak at less than about 20 microns or less than about 10, 5, 2 or 1 microns, or between about 1 and about 20 microns or between about 1 and 10, 1 and 5, 5 and 20, 10 and 20, 2 and 10 or 2 and 5 microns, e.g. about 1, 2, 3, 4, 5, 6, 7, 8, 9, 10, 11, 12, 13, 14, 15, 16, 17, 18, 19 or 20 microns. The bimodality may be due to some aggregation of particles of the substance to form loose aggregates.

The delivering may be at a rate of at least about 0.01 L/s, or at least about 0.05, 0.1, 0.5, 1, 2, 3, 4, 5, 6, 7, 8, 9, 10, 15 or 20 L/s, or between about 0.01 and 100, 0.1 and 100, 0.01 and 50, 0.01 and 10, 0.01 and 5, 0.01 and 1, 0.01 and 0.1, 0.1 and 10, 0.1 and 1, 1 and 100, 1 and 50, 1 and 25, 1 and 10, 1 and 5, 5 and 100, 20 and 100, 50 and 100, 5 and 50, 10 and 50, 25 and 50, 5 and 20 or 5 and 15 L/s, for example about 0.01, 0.05, 0.1, 0.2, 0.3, 0.4, 0.5, 0.6, 0.7, 0.8, 0.9, 1, 1.5, 2, 3, 4, 5, 6, 7, 8, 9, 10, 15, 20, 25, 30, 35, 40, 45, 50, 60, 70, 80, 90 or 100 L/s. In some circumstances the flow rate may be higher than this, for example about 150, 200, 250, 300, 350, 400, 450 or 500 L/s. The delivering may be under a pressure drop of at least about 20 bar, or at least about 25, 30, 35, 40, 45, 50, 55, 60, 65, 70, 75, 80, 85, 90, 95 or 100 bar, or between about 20 and 100 bar or between about 20 and 60, 20 and 50, 20 and 30, 30 and 100, 50 and 100, 30 and 70 or 40 and 60 bar greater, e.g. about 20, 25, 30, 35, 40, 45, 50, 55, 60, 65, 70, 75, 80, 85, 90, 95 or 100 bar. The flow rate may be such that the pressure drop along the nozzle is less than about 10 bar, or less than about 5, 2, 1, 0.5 or 0.1 bar or between about 0.01 and about 10 bar, or between about 0.01 and 5, 0.01 and 2, 0.01 and 1, 0.01 and 0.5, 0.1 and 10, 0.1 and 5, 0.1 and 2, 0.1 and 1, 1 and 10, 1 and 5 or 5 and 10 bar, e.g. about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9 or 10 bar. The delivering may be rapid, instantaneous or nearly instantaneous. It may occur within the space of about 0.1 and 500 ms, or between about 0.1 and 200, 0.1 and 100, 0.1 and 50, 0.1 and 10, 0.1 and 5, 0.1 and 2, 0.1 and 1, 1 and 100, 10 and 100, 50 and 100, 0.5 and 10, 0.5 and 5, 0.5 and 2, 1 and 50, 100 and 500, 200 and 500, 50 and 200, 10 and 200 or 1 and 10 ms, e.g. about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 100, 150, 200, 250, 300, 350, 400, 450 or 500 ms. The time for delivery of the solution into the supercritical fluid will depend on the nature (particularly the viscosity) of the solution, the nature (particularly the viscosity) of the supercritical fluid, the pressure difference between the solution and the supercritical fluid immediately prior to delivery and on other factors. The delivering may be sufficiently rapid for the solution to be distributed throughout the supercritical fluid following said delivering. The linear flow rate of the solution through the nozzle may be between about 10 and 500 m/s, or between about 10 and 200, 10 and 100, 10 and 50, 50 and 500, 100 and 500, 200 and 500, 50 and 200 or 100 and 200 m/s, e.g. about 10, 20, 30, 40, 50, 60, 70, 80, 90, 100, 150, 200, 250, 300, 350, 400, 450 or 500 m/s or may be less than about 10 or greater than about 100 m/s.

During the delivering, each shot of the solution may expand into a volume of the supercritical fluid of at least about 10 times the volume of the solution, or at least about 15, 20, 25, 30, 35 or 40 times the volume, or about 10, 15, 20, 25, 30, 35, 40, 45 or 50 times the volume of the solution, or between about 10 and 50, 20 and 50, 30 and 50, 10 and 40, 10 and 30, 20 and 40 or 25 and 35 times the volume of the solution.

The present invention aims in particular embodiments to achieve delivery of entire volume of working solution in a single rapid action. This enables the shortening of processing time by eliminating need to deliver working solution at low flowrates, as is common in existing processes. The release of working solution should be as highly energized as possible. Thus delivery of the working solution at very high flowrates through nozzles of relatively large apertures, as practiced in the present invention, develops atomized sprays. It is thought that concentration gradients are likely to be small, is negligible or absent if the working solution is sufficiently energetically distributed throughout the entire precipitation chamber. The rapid delivery techniques of the present invention commonly use compressed gas to introduce the working solution into the precipitation chamber in a single energetic step, i.e. in a single shot.

The ratio of the amounts of the solvent and the supercritical fluid may be such that the substance has low solubility in a mixture of the solvent and the supercritical fluid in said ratio. The ratio may be such that, under the conditions pertaining in the precipitation chamber following delivery of the solution into the supercritical fluid, the mixture of the solvent and the supercritical fluid in said ratio is in a supercritical state. Thus the mixture of the solvent and the supercritical fluid may following formation thereof, be both above the critical temperature and above the critical pressure for the mixture. Prior to the step of delivering, therefore, the supercritical fluid is preferably sufficiently far from its critical state that the mixture, which is formed during and immediately following the delivering, is in its supercritical state. The mixture should initially be a homogeneous or single phase mixture. The solubility of the substance in the mixture may be sufficiently low that at least about 80% of the substance present in the solution is precipitated, or at least about 85, 90, 91, 92, 93, 94, 95, 96, 97, 98, 99, 99.5 or 99.9% is precipitated, or in the range of between about 80 and 100% is precipitated, or between about 80 and 95, 80 and 90, 80 and 85, 85 and 100, 90 and 100, 95 and 100, 96 and 100, 97 and 100, 98 and 100, 99 and 100, 85 and 95 or 90 and 95% is precipitated. The solubility of the substance in the mixture, at the temperature and pressure following delivery, may be less than about 200 mg/l, or less than about 150, 100, 80, 60, 50, 40, 30, 20, 10, 5, 2 or 1 mg/L, or between about 0.1 and about 200 mg/L, or between about 0.1 and 100, 0.1 and 50, 0.1 and 20, 0.1 and 10, 0.1 and 5, 0.1 and 2, 0.1 and 1, 1 and 200, 10 and 200, 50 and 200, 100 and 200, 1 and 50, 1 and 20, 1 and 10, 1 and 5 or 5 and 50 mg/L, and may be about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 440, 45, 50, 60, 70, 80, 90, 100, 110, 120, 130, 140, 150, 160, 170, 180, 190 or 200 mg/L. The solubility may be less than about 1 mM, or less than about 0.5, 0.1, 0.05, 0.01, 0.005 or 0.001 mM, or may be between about 0.001 and 1 mM, or between about 0.001 and 0.1, 0.001 and 0.01, 0.01 and 1, 0.1 and 1, 0.01 and 0.1 or 0.005 and 0.05, e.g. about 0.001, 0.005, 0.01, 0.05, 0.1, 0.5 or 1 mM. The substance may be of low, negligible or zero solubility in the supercritical fluid. It may have a solubility of less than about 200 mg/l, or less than about 150, 100, 80, 60, 50, 40, 30, 20, 10, 5, 2 or 1 mg/L, or between about 0.1 and about 200 mg/L, or between about 0.1 and 100, 0.1 and 50, 0.1 and 20, 0.1 and 10, 0.1 and 5, 0.1 and 2, 0.1 and 1, 1 and 200, 10 and 200, 50 and 200, 100 and 200, 1 and 50, 1 and 20, 1 and 10, 1 and 5 or 5 and 50 mg/L, and may be about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 440, 45, 50, 60, 70, 80, 90, 100, 110, 120, 130, 140, 150, 160, 170, 180, 190 or 200 mg/L. The solubility may be less than about 1 mM, or less than about 0.5, 0.1, 0.05, 0.01, 0.005 or 0.001 mM, or may be between about 0.001 and 1 mM, or between about 0.001 and 0.1, 0.001 and 0.01, 0.01 and 1, 0.1 and 1, 0.01 and 0.1 or 0.005 and 0.05, e.g. about 0.001, 0.005, 0.01, 0.05, 0.1, 0.5 or 1 mM. If the substance is a mixture of components, each of the components may, independently, have a solubility as described above. The ratio of the solvent to the supercritical fluid may be for example less than about 1:10 on a volume basis, a weight basis or a mole basis, or less than about 1:15, 1:20, 1:25, 1:30, 1:35, 1:40, 1:45 or 1:50 e.g. about 1:10, 1:15, 1:20, 1:25, 1:30, 1:35, 1:40, 1:45 or 1:50 or between about 1:10 and about 1:50 or between about 1:10 and 1:40, 1:10 and 1:30, 1:10 and 1:20, 1:20 and 1:50, 1:30 and 1:50, 1:20 and 1:40 or 1:10 and 1:30, e.g. about 1:10, 1:15, 1:20, 1:25, 1:30, 1:35, 1:40, 1:45 or 1:50 e.g. about 1:10, 1:15, 1:20, 1:25, 1:30, 1:35, 1:40, 1:45 or 1:50. The supercritical fluid may be present in excess over the solvent on a volume basis, a weight or a mole basis. In this context the ratio should be determined by determining the volume of solvent in the solution prior to delivery into the supercritical fluid and comparing it with the volume of the supercritical fluid before delivery.

The process may additionally comprise the step of pressurising the solution with a gas to a pressure greater than that of the supercritical fluid before delivering the solution into the supercritical fluid. The gas should have low or negligible solubility in the solution or may be substantially insoluble therein, so that the solution does not undergo substantial expansion during pressurisation due to the gas. Suitable gases for pressurising a solution comprising a polar solvent include nitrogen, helium, neon or argon. "Substantially insoluble" in this context may involve less than about 10% v/v solubility, or less than about 5, 2, 1, 0.5 or 0.1% solubility, or between about 10 and 0.01%, 5 and 0.01, 1 and 0.01, 0.5 and 0.01, 0.1 and 0.01, 0.05 and 0.01 or 1 and 0.1%, e.g. about 0.01, 0.05, 0.1, 0.2, 0.3, 0.4, 0.5, 0.6, 0.7, 0.8, 0.9, 1, 2, 3, 4, 5, 6, 7, 8, 9 or 10% v/v solubility. The expansion of the solution may be less than about 10% volume expansion, or less than about 5, 2, 1, 0.5 or 0.1%. Under some circumstances the expansion may be greater than this, for example between about 10 and 50% or between about 10 and 20%. The expansion may be between about 0 and about 20%, or between about 0 and 10, 0 and 5, 0 and 2, 0 and 1, 0 and 0.5 or 0 and 0.2%, e.g. about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or 20%. The gas used for pressurising may be contained in a back-pressure chamber, said back-pressure chamber communicating with the injection chamber. The back-pressure chamber may be connected to a source of the gas, e.g. a gas cylinder. Alternatively the pressurising may employ some other means. For example the solution may be pressurised by means of a piston. Thus the injection chamber may be in the form of a cylinder having a piston fitted thereto. The solution may then be pressurised by application of a pressure (for example a hydraulic or mechanical pressure) to the piston. There may be a seal between the piston and the cylinder, said seal being capable of withstanding the maximum pressure used in the injection chamber without leakage. The seal should be resistant to the solution to be used in the injection chamber.

The pressurising may be to a pressure at least about 20 bar greater than the pressure of the supercritical fluid before delivering the solution into the supercritical fluid, or at least about 25, 30, 35, 40, 45, 50, 55, 60, 65, 70, 75, 80, 85, 90, 95 or 100 bar greater, or between about 20 and 100 bar greater or between about 20 and 60, 20 and 50, 20 and 30, 30 and 100, 50 and 100, 30 and 70 or 40 and 60 bar greater, e.g. about 20, 25, 30, 35, 40, 45, 50, 55, 60, 65, 70, 75, 80, 85, 90, 95 or 100 bar greater. The pressurising may be to a pressure of between about 100 and about 250 bar, or between about 120 and 250, 150 and 250, 200 and 250, 100 and 200, 100 and 150, 100 and 130, 120 and 200, 150 and 200 120 and 150 or 140 and 170 bar, e.g. about 100, 110, 120, 130, 140, 150, 160, 170, 180, 190, 200, 210, 220, 230, 240 or 250 bar. The pressure of the supercritical fluid before the delivering may be between about 50 and 200 bar, or between about 50 and 150, 50 and 100, 100 and 200, 150 and 200 or 100 and 150 bar, e.g. about 50, 60, 70, 80, 90, 100, 110, 120, 130, 140, 150, 160, 170, 180, 190 or 200 bar. Commonly the pressures in the injection chamber and the precipitation chamber during the process are controlled to a tolerance of about ±10 bar, or ±9, 8, 7, 6, 5, 4, 3, 2 or 1 bar. The temperature of the supercritical fluid may be such that the substance is not degraded, and such that the fluid is supercritical. It will therefore depend on the nature of the substance, the pressure and the nature of the supercritical fluid. Commonly the temperature will be between about 10 and about 60° C., or between about 20 and 60, 40 and 60, 10 and 40, 10 and 20, 20 and 50 or 30 and 50° C., e.g. about 10, 15, 20, 25, 30, 35, 40, 45, 50, 55 or 60° C. The apparatus of the invention may comprise a device for maintaining the desired temperature. This may be for example a bath, e.g. a water bath, and the bath should be provided with a is temperature controller. The bath (or other device for maintaining temperature) may maintain its temperature within about 2 Celsius degrees, or about 1.5, 1, 0.5, 0.2 or 0.1 Celsius degrees.

Conveniently, the step of delivering may comprise opening an injection valve so as to permit the solution to combine with the supercritical fluid. The injection valve should be capable of being opened rapidly in order to facilitate rapid delivery of the solution. It may for example be a ball valve, a solenoid valve or some other valve capable of rapid actuation. Thus under the pressure gradient between the solution and the supercritical fluid, the solution is rapidly propelled into the supercritical fluid, such that fine droplets are dispersed throughout the supercritical fluid. As the particles are formed from these droplets, the particles are formed throughout the mixture of the solvent and the supercritical fluid. This may lead to formation of very fine particles, with a relatively narrow particle size distribution. The particles may be less than about 100 nm mean diameter, or less than about 90, 80, 70, 60, 50, 40, 30 or 20 nm, or between about 20 and 100, 40 and 100, 60 and 100, 20 and 80, 20 and 60, 20 and 40, 20 and 60 or 30 and 50 nm or may be about 20, 30, 40, 50, 60, 60, 80, 90 or 100 nm mean diameter. They may have polydispersity (defined by weight average particle size divided by number average particle size) of less than about 5, or less than about 4, 3, 2.5, 2, 1.5, 1.4, 1.3 or 1.2. The particles may come together to form aggregates. The aggregates may be loosely bound aggregates. The aggregates may be less than about 20 microns in mean diameter, or less than about 15, 10, 5, 2 or 1 micron, or between about 1 and 20, 1 and 10, 1 and 5, 5 and 20, 10 and 20, 1 and 2, 2 and 5 or 5 and 10 microns, and may be about 1, 2, 3, 4, 5, 6, 7, 8, 9, 10, 11, 12, 13, 14, 1,5 16, 17, 18, 19 or 20 microns in diameter. They may have a ratio of d(0.9) to d(0.5), as measured by light scattering of between about 1.1 and 10, or between about 1.5 and 10, 2 and 10, 5 and 10, 1.1 and 2, 1.1 and 1.5 or 1.2 and 1.5, e.g. about 1.1, 1.2, 1.3, 1.4, 1.5, 1.6, 1.7, 1.8, 1.9, 2, 2.5, 3, 3.5, 4, 4.5, 5, 6, 7, 8, 9 or 10, or optionally more than 10.

During the delivering the pressure in the injecting chamber will increase, since the solution is initially at a higher pressure than the supercritical fluid. The pressure increase will depend on the pressure difference and relative volumes between the injection chamber and the precipitation chamber. The increase may be between about 1 and 10 bar, or between about 1 and 5, 1 and 2, 2 and 10, 5 and 10, 2 and 8 or 2 and 5 bar, e.g. about 1, 2, 3, 4, 5, 6, 7, 8, 9 or 10 bar.

The process may additionally comprise separating the particles from the mixture of the solvent and the supercritical fluid. The separating may comprise settling, centrifuging, filtering or some other process for separating. The step of separating is preferably conducted while maintaining the supercritical fluid in its supercritical state. This promotes separation of the solvent from the particles, so that when the particles are depressurised to ambient pressures, the particles may be substantially free of solvent. This prevents redissolution of the particles, and avoids any toxic effects that may be associated with the presence of the solvent on the particles. The process may additionally comprise washing the particles with the supercritical fluid before depressurising the particles. Thus after separating the particles from the supercritical fluid, additional supercritical fluid may be passed into the precipitation chamber and contacted with the particles. It may then be separated from the particles, as described above. This process may serve to remove traces of solvent remaining on the particles. The step of separation preferably involves filtration. This may be achieved using a frit or similar filter fitted to the outlet port of the precipitation chamber or fitted to a line leading from the outlet port of the precipitation chamber. Thus the frit or filter may be an in-line filter. The frit or filter should be inert to and insoluble in the supercritical fluid, and preferably to the solvent. It may for example comprise a sintered glass or metal frit. It may have a particle size cutoff of less than about 5 microns, or less than about 4, 3, 2, 1, 0.5 or 0.1 microns, or between about 0.1 and 5, 0.5 and 5, 1 and 5, 2 and 5, 0.5 and 5, 1 and 5 or 2 and 5, e.g. about 0.1, 0.2, 0.45, 0.5, 0.7. 1. 2, 3, 4 or 5 microns, depending on the size of the aggregates formed. There may be a valve, e.g. a needle valve, downstream from the filter or frit in order to allow flow through the filter or frit while maintaining supercritical conditions in the filter or frit.

The process may additionally comprise depressurising the particles to ambient pressure after said separating.

The term "supercritical fluid" as used herein refers to a fluid at or above its critical pressure $P_c$ and critical temperature $T_c$ simultaneously. The supercritical fluid will be maintained at a pressure of between about 1.01 to 10 times $P_c$, or 1.1 to 10, 1.2 to 10, 1.3 to 10, 1.4 to 10, 1.5 to 10, 1.6 to 10, 1.7 to 10, 1.8 to 10, 1.9 to 10, 2 to 10, 3 to 10, 4 to 10, 5 to 10, 1.01 to 5, 1.01 to 2, 1.01 to 1.5, 1.01 to 1.1, 1.01 to 1.05, 1.1 to 1 or 1.1 to 1.5 times $P_c$, e.g. about 1.01, 1.02, 1.03, 1.04, 1.05, 1.06, 1.07, 1.08, 1.09, 1.1, 1.15, 1.2, 1.25, 1.3, 1.35, 1.4, 1.45, 1.5, 1.6, 1.7, 1.8, 1.9, 2, 3, 4, 5, 6, 7, 8, 9 or 10 times $P_c$. It may be maintained at a temperature of between about 1.01 and 4 times $T_c$ (where $T_c$ is measured in Kelvin), or between about 1.1 to 4, 2 to 4, 3 to 4, 1.01 to 3, 1.01 to 2, 1.01 to 1.5, 1.01, to 1.1, 1.01 to 1.05, 1.1 to 1 or 1.1 to 1.5 times $T_c$, e.g. about 1.01, 1.02, 1.03, 1.04, 1.05, 1.06, 1.07, 1.08, 1.09, 1.1, 1.15, 1.2, 1.25, 1.3, 1.35, 1.4, 1.45, 1.5, 1.6, 1.7, 1.8, 1.9, 2, 3 or 4 times $T_c$. The supercritical fluid may comprise supercritical carbon dioxide or a mixture of supercritical carbon dioxide with an alcohol (e.g. methanol, ethanol, propanol, isopropanol, butanol or more than one of these.). If a mixture is used, it should be in a proportion such that the mixture forms a supercritical mixture. The mole fraction of the alcohol (or other modifier) in the carbon dioxide may be less than about 0.4, or less than about 0.3, 0.2, 0.1 or 0.05, or between about 0 and about 0.4 or between about 0 and 0.3, 0 and 0.2, 0 and 0.1, 0.1 and 0.4, 0.2 and 0.4 or 0.1 and 0.3 and may be about 0, 0.01, 0.05, 0.1, 0.15, 0.2, 0.25, 0.3, 0.35 or 0.4. Other supercritical fluids that may be used include supercritical nitrogen, nitrous oxide, sulfur hexafluoride, xenon, ethane, ethylene, chlorotrifluoromethane, chlorodifluoromethane, dichloromethane, trifluoromethane, helium, neon or a supercritical mixture of any two or more of these, or a supercritical mixture of any of these with carbon dioxide. The supercritical fluid may comprise a modifier in a suitable proportion that the fluid is supercritical under the conditions used in the present invention. The modifier may be for example an organic liquid, e.g. an alcohol, and ether, an ester or some other organic liquid. Advantages of the use of supercritical fluids in the invention include the fact that they have low viscosity. This allows for the very rapid mixing of the solvent and the supercritical fluid during particle formation. It is thought that this reduces the possibility of droplet coalescence, leading to small and relatively uniform particle sizes. The viscosity of the supercritical fluid may be less than about 0.1 cP, or less than about 0.05, 0.02, 0.01 or 0.005 cP, or between about 0.001 and about 0.1 cP or between about 0.001 and 0.01, 0.01 and 0.1, 0.005 and 0.05, 0.05 and 0.01 or 0.01 and 0.05, and may be about 0.001, 0.002, 0.003, 0.004, 0.005, 0.006, 0.007, 0.008, 0.009, 0.01, 0.015, 0.02, 0.025, 0.03, 0.035, 0.04, 0.045, 0.05, 0.06, 0.07, 0.08, 0.09 or 0.1 cP. For example the viscosity of supercritical carbon dioxide may be about 0.004 cP, and of supercritical carbon dioxide having about 0.3 mole fraction ethanol about 0.04 cP. A further advantage of the use of supercritical fluids is that, on reducing the pressure to ambient pressure, they may be converted to the gaseous state and thereby readily separated from the solid particles. The supercritical fluid should be a non-solvent for the substance from which the particles are made. It will be understood that most substances have a finite solubility in a solvent. In this context, the term "non-solvent" should be understood to mean that the solubility of the substance in the supercritical fluid is very low. It may be for example less than about 10 mg/L, or less than about 9, 8, 7, 6, 5, 4, 3, 2, 1, 0.5 or 0.1 mg/L and may be between about 0.1 and about 10 mg/L, or between about 0.01 and 5, 0.01 and 1, 0.01 and 5, 0.5 and 10, 1 and 10, 1 and 5 or 0.5 and 5, e.g. about 0.1, 0.2, 0.3, 0.4, 0.5, 0.6, 0.7, 0.8, 0.9, 1, 2, 3, 4, 5, 6, 7, 8, 9 or 10 mg/L. It may be sufficiently low that the particles of the substance may be washed with the supercritical fluid without loss of substantial amounts of particles (i.e. without loss of more than about 10% thereof, or less than about 5, 2, 1, 0.5, 0.2 or 0.1% thereof).

The solvent may be a polar solvent. It may be a non-aqueous solvent. It may be a dipolar aprotic solvent. It may be for example dimethyl sulfoxide, dimethyl formamide, N-methylpyrrolidone, hexamethyl phosphoramide, propylene carbonate, dichloromethane or some other solvent, or may be a mixture of any two or more of these. The solvent should be capable of dissolving the substance from which the particles are made. The solvent and the supercritical fluid may be miscible in the proportions in which they are present following delivery of the solution to the injection chamber, either as a single shot or in more than one shot. They may be miscible in all proportions or they may not be miscible in all proportions (i.e. they may be miscible in only some proportions).

The substance may be crystalline or non-crystalline or partially crystalline. It may be a mixture of substances or may be a pure substance. It may be organic or organometallic, polymeric, oligomeric or monomeric, hydrophilic, hydrophobic or amphiphilic. The substance may be or comprise a pharmaceutically active substance or a veterinarily active substance. It may a drug. It may be a protein, a peptide, a polysaccharide, an enzyme, an antibody, an antibody fragment or some other type of substance. The substance may be for example insulin or an analogue thereof, erythropoietin or an analogue thereof, epoietin or an analogue thereof; hydroxypropylated beta-cyclodextrin, Budesonide or EUDRAGIT™S100 (poly-(methacrylic acid-co-methyl methacrylate) 1:2). The substance may be used, or capable of being used, for the treatment of a condition in a patient, said treatment comprising inhaling said particulate substance, said substance being indicated for the treatment of the condition. The patient may be for example a human patient. The patient may be a mammalian patient. The patient may be a non-human mammalian patient e.g. a dog, a cat, a horse, a cow, a bull etc. The condition may be for example diabetes, asthma or some other condition which is treatable by inhalation of a particulate substance. The substance may be administered by inhalation, e.g. by nasal inhalation. Substances for nasal inhalation commonly do not require gastroresistant properties which are commonly required for substances administered intestinally. Substances for nasal inhalation commonly require a particle diameter of less than about 5 microns in order to reduce the mucociliary clearance, and to achieve a reproducible bioavailability of the nasally is administered substances. The present invention is not limited to any particular substance to be administered. The substance may be a therapeutic agent. The therapeutic agent may be any drug, biologically active peptide (monopeptide, dipeptide, oligopeptide or polypeptide e.g. hormones such as testosterone, nandrolene, menotropins, progesterone, insulin and urofolltropin, erythropoietin and epoietin, lymphokines such as interferon-alpha, interferon-beta, interferon-gamma, interleukin-1, interleukin-2, interleukin-4 and interleukin-8, globulins such as alpha-globulins, beta-globulins, gamma-globulins and immunoglobulin for example polyvalent IgG or specific IgG, IgA and IgM, e.g., anti-tetanus antibodies, albumins such as human serum albumin and ovalbumin), vaccine (e.g. peptide antigens and attenuated microorganisms and viruses, for example the B subunit of the heat-labile enterotoxin of enterotoxigenic *E. coli*, the B subunit of cholera toxin, capsular antigens of enteric pathogens, fimbriae or pili of enteric pathogens, HIV surface antigens, dust allergens and acari allergens), or any other moiety. Examples of drugs which can be used in the present invention include drugs which act on the cardiovascular system (e.g. lidocaine, adenosine, dobutamine, dopamine, epinephrine, norepinephrine, phentolamine), drugs which act on the central nervous system (e.g. doxapram, alfentanil, dezocin, nalbuphine, buprenorphine, naloxone, ketorolac, midazolam, propofol, metacurine, mivacurium, succinylcholine), antineoplastic drugs (e.g. cytarabine, mitomycin, doxorubicin, vincristine, vinblastine) and antibiotics (e.g. methicillin, mezlocillin, piperacillin, cetoxitin cefonicid, cefmetazole and aztreonam). When the therapeutic agent is insulin, the particulate substance of the present invention may be useful for the treatment of diabetes. The quantity of the substance administered to the patient may vary depending upon the particular substance, the disease or condition being treated, as well as the age, weight and sex of the subject being treated.

The substance may in some embodiments be a herbicide, a pesticide, a rodenticide, a fungicide or some other substance.

The process of the invention may be used to form coated particles. The particles may be partially coated. They may be completely coated. They may be coated by an encapsulant. They may be at least partially encapsulated by the encapsulant. Such particle may be made by different embodiments of the invention.

In one embodiment the process comprises delivering a dispersion of core particles in a solvent, said dispersion comprising the encapsulant in solution, into a supercritical fluid, said supercritical fluid being a non-solvent for the core particles and for the encapsulant and being miscible with the solvent. The particles as they are formed are distributed in a mixture of the solvent and the supercritical fluid. Thus, as the dispersion is injected in to the supercritical fluid, the encapsulant forms a coating, or a partial coating, surrounding the core particles. The dispersion may be a suspension. It may be a colloidal dispersion. The ratio between the core particles and the encapsulant in the dispersion may be between about 1:20 and about 20:1 on a weight or mole basis. It may be about 1:10 and 10:1, 1:5 and 5:1, 1:2 and 2:1, 1:20 and 1:1, 1:1 and 20:1, 1:5 and 1:1 or 1:1 and 5:1, for example, and may be about 20:1, 10:1, 5:1, 4:1, 3:1, 2:1, 1.5:1, 1:1, 1:1.5, 1:2, 1:3, 1:4, 1:5, 1:10 or 1:20, or may be some other desired ratio. This embodiment is useful for core particles that are difficult to dissolve in a suitable solvent. These core particles include inorganic particles, such as salts, metals, e.g. iron oxide, iron etc. The encapsulant in this case may be a polymeric material, or it may be as described for the substance earlier that may be made into particles according to the present invention.

In another embodiment, the core particles are produced using the process of the invention. Thus a suitable process comprises delivering a first solution, comprising the substance dissolved in a first solvent, into a supercritical fluid, said supercritical fluid being a non-solvent for the substance and being miscible with the first solvent. This results in formation of core particles of the substance, said particles being distributed in a mixture of the solvent and the supercritical fluid. A second solution, comprising an encapsulant dissolved in a second solvent, is then delivered into the supercritical fluid having the particles distributed therethrough, said supercritical fluid being a non-solvent for the encapsulant and being miscible with the second solvent. This then results in formation of a coating (partial or complete) of the encapsulant on at least some of the particles of the substance. Thus in this embodiment the core particles are formed in situ using the process of the invention, and the process is then used again in order to form the coating of encapsulant. Ratios of substance and encapsulant are as described for the earlier embodiment for forming coated particles. This embodiment may be suitable for producing coated particles in which the core particles comprise a substance that may be readily dissolved in suitable solvents. It may be used for example for applying a slow release, or controlled release, coating onto particles of a drug. In this case, a suitable coating may be a polymer capable of controlling release of the substance of the core particles.

A suitable apparatus for producing particles of a substance using the above method comprises a pressurisable injection chamber and a precipitation chamber. A conduit connects the injection chamber and the precipitation chamber, and is fitted with an is injection valve such that when the valve is open the injection chamber communicates with the precipitation chamber and when the valve is closed the injection chamber is isolated from the precipitation chamber. The precipitation chamber should be capable of maintaining supercritical conditions (temperature and pressure) for a supercritical fluid. Thus the precipitation chamber may have a temperature controller. This may be an electrical controller, or may comprise a heated bath (e.g. water bath) in which the precipitation chamber may be at least partially immersed. The precipitation chamber should have an inlet, which may be coupled to a source of the supercritical fluid, and an outlet port for permitting egress of supercritical fluid.

The conduit may be a tube or a pipe. It comprises an injection valve so that when the injection valve is open a liquid may pass through the conduit and when the injection valve is closed no liquid may pass through the conduit.

Thus when the injection chamber is loaded with the solution and pressurised to greater than the pressure in the precipitation chamber with the valve closed, opening the valve leads to a very rapid expulsion of the solution from the injection chamber into the precipitation chamber, thereby forming a fine spray of the solution throughout the precipitation chamber.

It is convenient in the present invention to use a precipitation chamber with a relatively wide access neck, to allow for visualization of precipitate deposition and hence of the spray pattern of working solution. Wide access also facilitates precipitate recovery.

In an embodiment, the precipitation chamber comprises a port for introduction of supercritical fluid, a port for introduction of the working solution (i.e. the conduit), a port for pressure monitoring and a port for discharge of supercritical fluid from the chamber.

The injection chamber may be constructed from any suitable material that is physically and chemically resistant to the conditions and materials used in the process. A suitable material is 12.57 mm O.D. stainless steel tubing. The length of tubing may be selected to contain the desired volume of working solution, e.g. 10 ml.

The internal surface of the injection chamber is preferably smooth to minimize retention of the working solution along the sides of the chamber sides, thereby facilitating delivery of the maximum amount of solution into the precipitation chamber. Thus the internal surface of the injection chamber may be polished to a high mirror finish.

The injection chamber and precipitation chamber should be capable of withstanding sudden pressure changes, and should be constructed accordingly. Suitably, a 300 ml bolt closure vessel is capable of withstanding pressure shock and may be used as the precipitation chamber.

It has been found that increasing the volume of gas used for pressurising the working solution decreases the pressure required for its energized delivery, since at constant mass of back-pressure gas required, a smaller contained volume implies a higher pressure. Also, by maximizing the volume of gas, there is less need to control the pressure within the back-pressure chamber. In one practical embodiment of the invention a 150 ml back-pressure chamber (Whitey 150 ml sample cylinder) was coupled directly to the injection chamber.

It is preferable that the back-pressure gas does not liquefy within required operating pressures (for example within the range of about 1 to about 200 bar at 25° C. to 40° C.). Also, the back-pressure gas should not interact with the working solution, and the working solution (in particular the solvent) should not evaporate excessively into the gas. Nitrogen has low solubility in the liquid phase of many organic solutions, and the solubility of organic vapours in nitrogen (evaporation) decreases as pressure increases. Therefore at high pressures as used in the injection chamber evaporation of solvent into nitrogen gas is expected to be low as required. Accordingly, nitrogen is a suitable back-pressure gas for use in the present invention.

The apparatus may additionally comprise a separation device for separating the particles from the mixture of the solvent and the supercritical fluid while maintaining the supercritical fluid in its supercritical state. As noted above, this may comprise a filter, e.g. a frit, for filtering the particles. It should also comprise suitable valves and/or pressure controllers to allow the separation to occur under supercritical conditions for the fluid. The apparatus should be designed so that the filter is accessible, so as to allow recovery of the particles so filtered from the supercritical fluid. This may be by means of a screw fitting or similar.

The apparatus may comprise a pressuriser for pressurising the injection chamber. This may for example comprise a high pressure source of a gas that is of low solubility in the solvent. The injection chamber should also have means for admitting the solution thereto. This may be for example an openable insertion port, or may comprise a resealable septum port or may be any other suitable means.

The conduit may extend into the precipitation chamber. It may extend between about 5 and 50 mm into the chamber, although this distance does not appear to be critical. It may extend about 5 and 30, 5 and 20, 5 and 10, 10 and 50, 20 and 50, 30 and 50 or 20 and 40 mm into the chamber, e.g. about 5, 10, 15, 20, 25, 30, 35, 40, 45 or 50 mm. The is minimum internal diameter of the conduit may be sufficiently large to allow single shot delivery of the solution into the supercritical fluid. It may be sufficiently large to allow rapid, instantaneous or near instantaneous delivery of the solution into the supercritical fluid. Commonly the diameter will be between about 0.5 and 2 mm in diameter, or between about 0.5 and 1.5, 0.5 and 1, 1 and 2 or 1 and 1.5 mm, e.g. about 0.5, 0.6, 0.7, 0.8, 0.9, 1, 1.1, 1.2, 1.3, 1.4, 1.5, 1.6, 1.7, 1.8, 1.9 or 2 mm. The diameter should be sufficiently large to allow for the rapid expulsion of the solution into the precipitation chamber as described earlier. An advantage of the present invention is that atomization of the working solution can occur without use of a capillary nozzle (as is used in some existing devices). High nucleation density that typically occurs at capillary nozzle tips can lead to a high bulk density product. Additionally, the absence of a capillary nozzle improves scalability of process by removing effect of nozzle spray during process intensification (i.e. optimisation or scale-up). In some embodiments of the present invention, the injection chamber is coupled directly onto the top of the precipitation chamber and is connected thereto by a ball valve. This arrangement minimizes bends in the conduit which would otherwise result in losses in energy of flow of the working solution as it passes from the injection chamber to the precipitation chamber. Thus the conduit may be a straight or substantially straight conduit. It may have no bends therein.

The volume of the precipitation chamber may be at least about 10 times the volume of the injection chamber. The ratio between the volumes of the injection chamber and the precipitation chamber may be between about 10 and about 50, or between about 10 and 40, 10 and 30, 10 and 20, 20 and 50, 30 and 50 or 20 and 40, and may be about 10, 15, 20, 25, 30, 35, 40, 45 or 50. In some embodiments the injection chamber is between about 2 and about 20 $cm^3$ volume, or between about 2 and 10, 2 and 5, 5 and 20, 10 and 20, 5 and 15 or 8 and 12 $cm^3$, e.g. about 2, 3, 4, 5, 6, 7, 8, 9, 10, 11, 12, 13, 14, 15, 16, 17, 18, 19 or 20 $cm^3$. The volume of the precipitation chamber may be between about 200 and 500 $cm^2$, or between about 200 and 400, 200 and 300, 300 and 500, 400 and 500, 250 and 400 or 250 and 350 cm³, e.g. about 200, 250, 300, 350, 400, 450 or 500 cm³.

In order to scale the apparatus up for larger production volumes, the apparatus described above may be replicated a number of times. Thus to increase the production rate by a factor of x, the apparatus described above may be replicated x times. Alternatively, multiple (i.e. x) injection chambers as described above may be connected to a single precipitation chamber by multiple (i.e. x) conduits, wherein the precipitation chamber has a volume of about x times larger than that used with a single injection is chamber. As another alternative, a single injection chamber, having volume about x times larger than that used with a single precipitation chamber, may be connected using multiple (i.e. x) conduits to multiple precipitation chambers. In this instance, x may be any desired multiple. It may be from 2 to 1000 or more, depending on the desired rate of production. It may be from 2 to 500, 2 to 100, 2 to 50, 2 to 20, 10 to 1000, 100 to 1000, 500 to 1000, 100 to 500 or 100 to 200, e.g. about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900 or 1000.

The particulate substance of the present invention may have a mean particle size of between about 10 and 200 nm, or between about 20 and 200, 50 and 200, 100 and 200, 10 and 150, 10 and 100, 10 and 50, 10 and 40, 20 and 100, 20 and 50 or 20 and 40 nm, e.g. about 10, 15, 20, 25, 30, 35, 40, 45, 50, 60, 70, 80, 90, 100, 110, 120, 130, 140, 150, 160, 170, 180, 190 or 200 nm. The particulate substance may have a bimodal particle size distribution. The smaller of the two modes may be as described above for the mean particle size. The larger of the two modes may be as described below for the aggregates. The particulate substance may comprise a drug for pulmonary delivery. The particulate substance may have a bulk density between about 1 and about 50 mg/ml or between about 5 and 20, 1 and 30, 1 and 20, 1 and 10, 1 and 5, 5 and 50, 10 and 50, 20 and 50, 5 and 30 or 5 and 10 mg/ml, e.g. about 1, 2, 3, 4, 5, 6, 7, 8, 9, 10, 15, 20, 25, 30, 35, 40, 45 or 50 mg/ml. The particulate substance may have a specific surface area of greater than about 10 m²/g or greater than about 15, 20, 25, 30, 35 or 40 m²/g, or between about 10 and 100 m²/g or between about 10 and about 50 m²/g or between about 10 and 40, 10 and 30, and 50, 30 and 50, 20 and 40, 50 and 100 or 25 and 35 m²/g, e.g. about 10, 15, 20, 25, 30, 35, 40, 45, 50, 60, 70, 80, 90 or 100 m²/g. It may be in the form of loose aggregates having a mean diameter of less than about 20 microns or less than about 10, 5, 2 or 1 microns, or between about 1 and about 20 microns or between about 1 and 10, 1 and 5, 5 and 20, 10 and 20, 2 and 10 or 2 and 5 microns, e.g. about 1, 2, 3, 4, 5, 6, 7, 8, 9, 10, 11, 12, 13, 14, 15, 16, 17, 18, 19 or 20 microns.

The particles of the particulate substance may be spherical, polyhedral (with between about 6 and about 50 sides), irregular shaped, ovoid, acicular, platelet-shaped, oblate spheroid or some other shape.

The present invention provides inherent benefits associated with operating dense gases under high pressure. Products precipitated using the process of the invention may be sterilized in-situ, as a result of high pressures used in the process. The absence of oxygen during precipitation of the produce may serve to inhibit, reduce or eliminate oxidative degradation of the particles. Thus the process may be performed under substantially anoxic conditions. Foaming of semi-solid matrices may also be performed during pressure release following particle formation, when dense gases revert to the gaseous phase.

Key characteristics of the present process include:

Using a pressure differential, a volume of working solution containing dissolved pharmaceutical compound(s) is completely delivered into a sealed vessel containing antisolvent;

Delivery of the solution is uncontrolled and the duration of the delivery is almost instantaneous, if not instantaneous;

The pressure differential is used to energetically atomize the working solution during delivery, eliminating the use of capillary nozzles;

The working solution is not substantially pre-expanded prior to delivery;

Rapid delivery of the working solution allows for a reduction in operating times;

An excess volume of antisolvent is used—when the working solution is delivered, it is distributed into the entire vessel containing antisolvent, achieving a homogeneous mixture of working solution and antisolvent with a much lower working solution concentration in the vessel;

This lower working solution concentration in the vessel allows the formation of precipitate with much lower bulk densities;

With the almost instantaneous delivery of the entire volume of working solution, localized effects of solvent extraction are minimized, with the entire bulk of working solution experiencing the same level of solvent extraction, allowing for product with more uniform characteristics (tighter particle size distribution);

Absence of capillary nozzles and, as a consequence, absence of the effect of changing spray patterns due to different flowrates through capillary nozzles contribute to the higher degree of scalability of process.

Similar to the GAS and the ASES process, the present process utilizes the anti-solvent abilities of a supercritical nonsolvent such as $CO_2$ to effect the precipitation of previously dissolved compounds from a solvent. The energized rapid release of solutions into an antisolvent environment media of the present process however, offers a fundamental advantage over other processing platforms. Operating characteristics of the above-mentioned processes are briefly compared in Table 1.

TABLE 1

Operating characteristics of various SCF particle formation processes.

| Process | Solvent | Anti-solvent | Atomizer | Precipitation Mechanism |
|---|---|---|---|---|
| RESS | $CO_2$ | Nil | Capillary Nozzle/ Orifice | Pressure and Temperature Reduction |
| GAS | Organic Solvent | $CO_2$ | Sintered Frit | Anti-solvent |
| ASES | Organic Solvent | $CO_2$ | Capillary Nozzle/ Orifice | Anti-solvent |
| DELOS | $CO_2$ and Organic Solvent | Nil | Pressure Differential | Temperature Reduction |
| ARISE | Organic Solvent | $CO_2$ | Pressure Differential and 1 mm ID Tubing | Anti-solvent |

Example

Materials and Method

A schematic of the apparatus used in the examples is presented in FIG. 1. In FIG. 1, nitrogen cylinder 1 and carbon dioxide cylinder 2 are provided for supplying gases to the apparatus. Syringe pumps 3 and 3' are provided for pressurising the nitrogen and carbon dioxide respectively. Cylinder 1 is connected to syringe pump 3 by ball valve V1, which is capable of isolating cylinder 1 from syringe pump 3. Similarly cylinder 2 is connected to syringe pump 3' by ball valve V3, which is capable of isolating cylinder 21 from syringe pump 3'. Heating coil 4 is provided for heating the compressed carbon dioxide to the desired temperature for use. Valve V4 and check valve V4' are provided between syringe pump 3' and coil 4 to open or close the connection between pump 3' and coil 4, and to prevent backflow of carbon dioxide into syringe pump 3'. Back pressure chamber 5 is provided as a reservoir of compressed nitrogen for pressurising the working solution prior to delivery. Valve V2 and check valve V2' are provided between syringe is pump 3 and back-pressure chamber 5 to open or close the connection between pump 3 and chamber 5, and to prevent backflow of carbon dioxide into syringe pump 3. Injection chamber 6 is connected to back pressure chamber 5, and is fitted with pressure transducer P1 for determining the pressure in chamber 5, and with valve V5 for admitting the working solution to injection chamber 6 and for closing off back pressure chamber 5 and injection chamber 6 from the atmosphere. Precipitation chamber 7 has port 7', connected to coil 4, for admitting supercritical carbon dioxide to chamber 7. Chamber 6 communicates with chamber 7 via ball valve V6, which is connected to nozzle 8, which extends into chamber 7. Chamber 7 is also fitted with pressure transducer V2 for determining a pressure within chamber 7. Outlet 7" to chamber 7 is connected to needle valve NV via in-line filter 9, which is provided to collect the precipitated product. Filter 9 is openable and resealable so as to access the product made in the apparatus. Needle valve NV is provided to ensure that the pressure in in-line filter 9 is sufficient to maintain the mixture from chamber 7 at supercritical conditions while filtering out the product. Solvent trap 10 is connected to needle valve NV in order to trap solvent which returns to the liquid state when the mixture of supercritical fluid and solvent is returned to non-supercritical conditions. The outlet from trap 10 is vented to waste. Water heater 11 and water bath 12 are provided for maintaining critical components of the apparatus at the desired temperature. Thus in operation those portions of the apparatus which are required to contain supercritical fluid are immersed in water bath 12 in order to ensure that correct supercritical temperatures are maintained.

Wetted parts were all of Grade 316 stainless steel construction. A 300 ml bolt closure vessel (Autoclave Engineers) was used as precipitation chamber 7 while injection chamber 6 was fashioned out of a length of 12.7 mm tubing. The internal volume of injection chamber 6 was about 10 ml. 150 ml sample cylinder 5 (Whitey) was connected directly to injection chamber 6 with 6.4 mm tubing to provide back-pressure during solution delivery. The injection chamber 6 and precipitation chamber 7 were connected by 3.2 mm tubing with internal diameter of about 1 mm. The 3.2 mm inch tubing extended past the cap of precipitation chamber 7 by about 30 mm, functioning as a nozzle (8) during solution delivery. The contents of both chambers were separated with a ball valve V6. Internal pressures of injection chamber 6 and precipitation chamber 7 were separately monitored by two pressure transducers (Druck) P1 and P2 respectively. Critical components of the process were immersed in temperature controlled water bath 12 which was held at 40° C.

Chemicals and Compounds

| Chemical | Supplier | Lot No. | Purity |
|---|---|---|---|
| Carbon Dioxide | Linde Aust. | — | $\geq$99.5% |
| Nitrogen | Linde Aust. | — | $\geq$99.999% |
| Methanol | Ajax Finechem Aust. | 403041 | $\geq$99.7% |
| Ethanol | Merck Aust. | 36739 | $\geq$99.7 |
| Acetone | Ajax Finechem Aust. | AH310108 | $\geq$99.5% |
| Dimethyl Sulfoxide | Ajax Finechem Aust. | AH412153 | $\geq$99.9% |
| Deionized Water | From Milli-Q Academic Water Purification System | — | 18.2 M$\Omega \cdot$cm |
| EUDRAGIT ™ S100 (poly-(methacrylic acid-co-methyl methacrylate) 1:2) | Degussa GmbH Pharma Polymere | 0490305044 | — |
| Hydroxy-Propylated beta-Cyclodextrin | Wacker-Chemie GmbH | — | $\geq$ |
| Bovine Insulin | Sigma-Aldrich GmbH | 054K1375 | 28 USP units/mg (HPLC) |
| Human Insulin | Biocon Limited | B-0510741C/00073 | 99.3% |
| $Fe_3O_4$ Iron Oxide Nanoparticles | Nanomaterials Pte. Ltd | NMT-Fe-070806-1 | — |

Off-the-shelf Equipment (Drawing Numbers Refer to FIG. 1)

| Drawing No. | Equipment | Manufacturer/Model |
|---|---|---|
| 3. | Syringe Pump | Isco Model 500D, 500 ml capacity |
| 7. | 300 ml Autoclave | Autoclave Engineers Inc. 300 ml Bolt Closure Vessel |
| P1, P2 | Pressure Transducer | Druck, zero to 350 bar |
| $V_n$ | Ball Valve (also used to isolate injection chamber from Precipitation Vessel) | Swagelok, Series 41, SS-41S2, minimum orifice diameter 2.4 mm |

Custom-built Equipment

| 1.0 mm I.D. Nozzle | | |
| --- | --- | --- |
| Material | Dimensions | Part No. |
| 316 SS | Length: 100 mm<br>O.D.: 3.175 mm<br>I.D.: 1.0 mm | — |
| 0.762 mm I.D. Nozzle: 1.0 mm I.D. Nozzle plus the parts listed below | | |
| Stainless Steel | — | Reducing Union<br>Swagelok SS-200-6-1 |
| Stainless Steel | Length: 17.272<br>O.D.: 1.588 mm<br>I.D.: 0.762 mm | Port Connector<br>Swagelok SS-101-PC |

* Nozzle was cut from length of tubing; ends were squared, burr-free and polished to ensure symmetrical delivery pattern.
Total Length of 0.762 mm I.D. Nozzle = 124.4 mm

| Injection Chamber | | |
| --- | --- | --- |
| Material | Dimensions | Part No. |
| Top Cap | | |
| Stainless Steel | — | Reducing Union<br>Swagelok SS-810-6-4 |
| Bottom Cap | | |
| Stainless Steel | — | Reducing Union<br>Swagelok SS-810-6-2 |
| Body | | |
| Stainless Steel | Length: 150 mm<br>O.D.: 12.7 mm<br>I.D.: 9.56 mm | — |

* Internal bore of Body was polished to a high mirror finish to reduce clinging of working solution onto surface (retention) during delivery.

Volume of back-pressure chamber and injection chamber circuit: 182.0±0.6 ml
Volume of precipitation vessel circuit: 355.3±1.3 ml
Solution Preparation:
  Weighted amount of compound is loaded into a clean 50 ml glass vial;
  Metered amount of solvent is added into the 50 ml glass vial;
  Glass vial is immersed in an ultrasound bath for 15 minutes to completely dissolve compound If necessary;
  Compound is ascertained to be completely dissolved when a clear solution is achieved.
Preparation of Insulin in Acidified Deionized Water Solution:
  Weighted amount of insulin is loaded into a clean 50 ml glass vial;
  5 ml of deionized water is added into the 50 m glass vial;
  To raise the solubility of insulin in water, 14 drops of 0.1N HCl is added gradually while agitating the 50 ml vial to acidify the solution;
  After a clear solution is achieved, 2 drops of 1.0N NaOH is introduced into the 50 ml vial while agitating to obtain a solution with a pH of about 5.
Preparation of Carbon Dioxide Expanded Ethanol Antisolvent System:
  The amount of ethanol required to prepare the antisolvent system is added into the precipitation chamber just before the precipitation chamber is assembled;
  Carbon dioxide at 50 bar is added into the apparatus and the apparatus is subsequently depressurized from the top to purge the apparatus of atmospheric air;
  Carbon dioxide is next added from the bottom of the precipitation chamber to expand the ethanol as it condenses into the ethanol phase. Operating pressures and temperatures selected for experimentation have all corresponded to the achievement of single phase systems, i.e. the absence of a liquid and vapor phase within the precipitation chamber;
  Additional carbon dioxide is added into the precipitation chamber as necessary and the system is left to stand overnight (excessive duration) to attain equilibrium;
General Method
  The precipitation chamber 7 is filled with $CO_2$ to stipulated experimental conditions and subsequently depressurized to purge the system with $CO_2$ and to check the system for leaks;
  To prepare the antisolvent system in the ARISE process, the precipitation chamber is charged with:
    Either carbon dioxide to achieve stipulated experimental conditions; or
    Carbon dioxide modified with ethanol as previously described.
  Antisolvent system is given time to attain equilibrium, 30 minutes for $CO_2$ and overnight for $CO_2$ modified ethanol;
  Working solution prepared as previously described is introduced into injection chamber 6 with a syringe;
  Nitrogen is added into back-pressure chamber 5 and injection chamber 6 to a pressure in excess of precipitation chamber 7, typically 50 bar in excess;
  Back-pressure chamber 5 and injection chamber 6 were given 5 minutes to attain constant pressure;
  $V_6$ was flicked open for a period of 5 seconds;
  The entire process was allowed to rest for 10 minutes for pressures to stabilize;
  The stipulated volume of $CO_2$ was next passed through precipitation chamber 7 under isobaric and isothermal conditions at constant flowrate to flush the vessel of residual solvent;
  Precipitate was retained in the precipitation chamber with a 0.5 micron stainless steel filter at the base;
  Precipitation chamber 7 was disconnected from the system and disassembled to recover precipitate. During disassembly, vessel was handled carefully and not inverted to minimize disturbance to precipitate deposition within precipitation chamber 7;
  Injection chamber 6 was disconnected and disassembled to inspect for any working solution retained; very tiny amounts (~0.05 ml) were retained in very rare cases.
Particular Method
  In this example, 200 mg of Insulin (Bovine Pancreas—Sigma-Aldrich or Human Recombinant Insulin—Biocon Limited) was dissolved in 10 ml dimethyl sulfoxide (DMSO 99.5%—AJAX Finechem) to form a working solution. After purging the precipitation chamber 7 of air with $CO_2$ (99.5%—Linde), $CO_2$ was introduced into the precipitation chamber 7 through a spiral heating coil 4 with a syringe pump 3 (ISCO 500D) to the desired working pressure; the chamber 7 was then sealed. Working pressures selected in this study were above the saturation pressure of the $CO_2$/DMSO system. The precipitation chamber 7 was allowed 30 mins to achieve equilibrium. The working solution was next introduced into the injection chamber 6 with a syringe through $V_5$. The injection chamber 6 and back-pressure vessel 5 were then charged with nitrogen (99.999%—Linde) to a pressure 50 bar in excess of the precipitation vessel 7 and sealed. Nitrogen was used to achieve the pressure differential because of its low solubility in the working solution so as to prevent undesirable expansion and precipitation prior to delivery.

Figure 11:
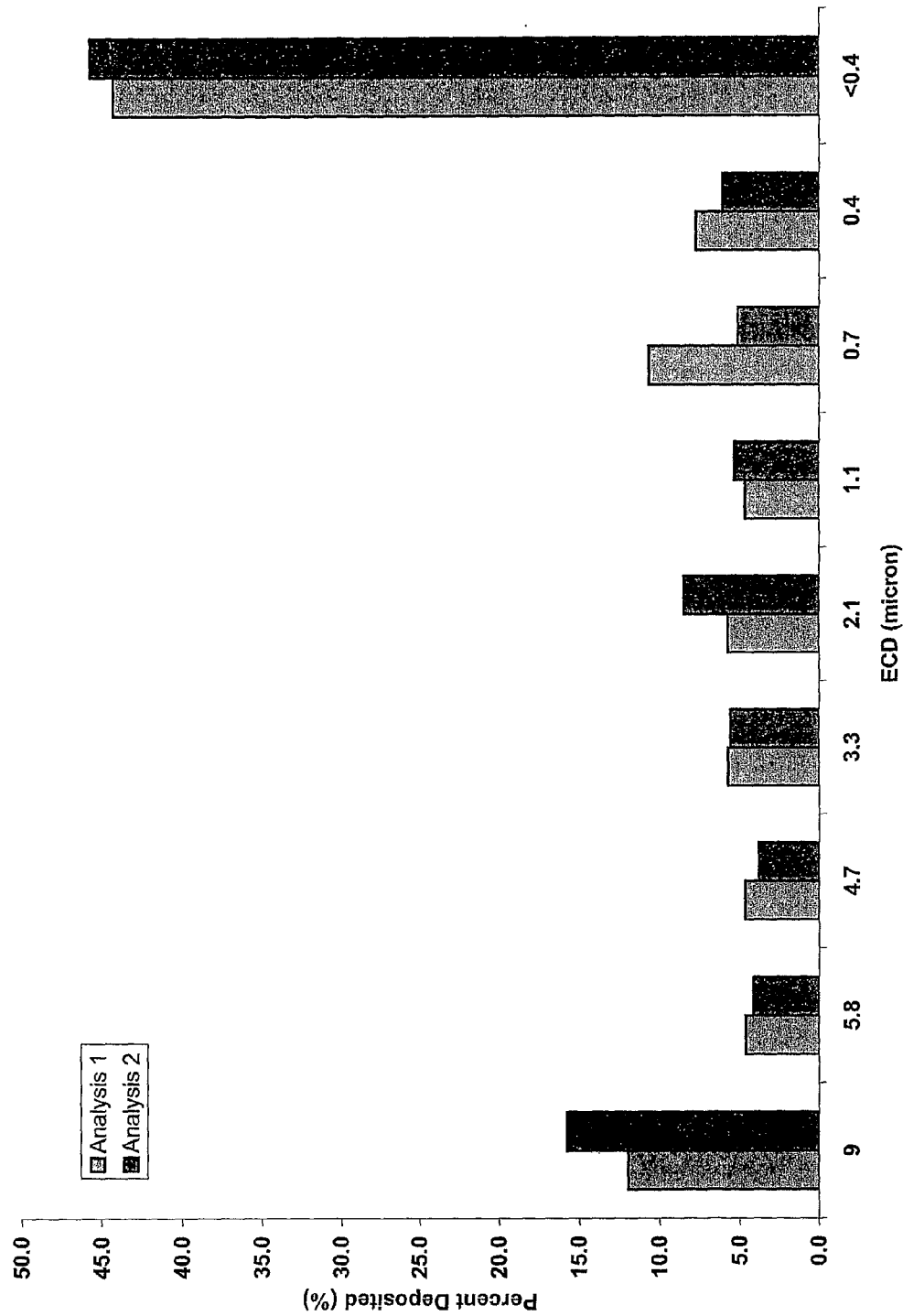
FIG. 11 shows a graph showing results of in-vitro inhalability testing of insulin particles produced by the process of the present invention.

By quickly opening $V_6$ for a period of 5 seconds, the working solution was energetically delivered into the precipitation chamber 7 through the 3.2 mm tubing 8. Upon opening $V_6$, the injection chamber 6 experienced an abrupt depressurization as its contents were emptied into the precipitation vessel 7 almost instantaneously. The pressure of the precipitation chamber 7 experienced a simultaneous increase. The contents of the precipitation chamber 7 were then allowed to rest for 10 minutes to achieve a stable pressure. $CO_2$ was next passed through the precipitation chamber 7 under isobaric and isothermal conditions to flush the system of DMSO. Precipitate was retained in the precipitation chamber 7 with a 0.5 micron frit at the base, while allowing extracted solvent and antisolvent to exit the precipitation chamber 7.

Results and Discussion

Experimental conditions and the particle size distributions of five ARISE experiments are summarized in Table 2. Particle size distributions of powders were obtained from light scattering (Malvern Mastersizer 2000) using ethanol as a dispersant. All runs were conducted at 40° C., with 10 ml of working solution containing 200 mg of insulin and with the initial pressure of the injection chamber at a 50 bar excess.

TABLE 2

Experimental conditions and results of ARISE precipitation of Insulin.

| Case | Precipitation Vessel Pressure (bar) | | Light-Scattering Results (μm) | | |
|---|---|---|---|---|---|
| No. | Pre -Delivery | Post - Delivery | d(0.1) | d(0.5) | d(0.9) |
| 1 | 90 | 97.1 | 3.875 | 6.318 | 10.134 |
| 2 | 120 | 124.7 | 0.082 | 0.245 | 1.942 |
| 3 | 120 | 124.7 | 0.083 | 0.253 | 2.282 |
| 4 | 120 | 124.7 | 0.083 | 0.250 | 2.103 |
| 5 | 150 | 158.4 | 0.081 | 0.239 | 2.532 |

The five ARISE experiments demonstrate the ability of the process to precipitate micron and even submicron sized particles of insulin. The similar particle size distributions obtained with cases 2, 3 and 4 validate the reproducibility of the process. The contrasting conditions between case 1, 2 and 5 also illustrate the tunable nature of the process—product characteristics were easily altered simply by varying the initial pressure of the precipitation chamber.

Electron microscope images (Hitachi S900) of product from case 4 reveal insulin recovered from the ARISE processing consist of highly aggregated sub-micron individual particles.

The powders obtained from all five cases were observed to have undergone a dramatic reduction in bulk density. The low bulk density of the product was believed to be the result of precipitation occurring within the entire volume of the precipitation chamber and not at a localized interface as experienced with ASES and its derivative platforms. With the high energy release of the working solution during delivery, the working solution would invariably be distributed throughout the entire precipitation chamber.

Conclusion

The micronization of insulin was successfully demonstrated with the newly developed ARISE process. The ARISE process is fundamentally different from existing processes in that it exploits a pressure differential and rapid delivery techniques to energetically atomize a working solution into an anti-solvent without the use of capillary nozzles. By harnessing the inertia of the working solution to intensify mixing, precipitation was made to occur within the entire volume of the precipitation chamber. It is believed that this is what imparts the characteristically low bulk densities to powders processed with the ARISE process.

The figures provided show various aspects of the process, apparatus and products described in the example or related processes. FIG. 2 shows electron micrographs of particulate insulin produced using the process of the present invention. The three is micrographs, at different magnifications, show the loose aggregates of particles that are produced by the process, and at higher magnifications the primary particles may be seen, showing that they have a relatively narrow particle size distribution.

FIGS. 3 to 6 show schematics of portions of the apparatus used. Thus FIG. 3 shows a 1.0 mm ID nozzle for use as nozzle 8 of FIG. 1. The ends of the nozzle are polished and free of burrs in order to facilitate smooth delivery of the solution to the precipitation chamber. FIG. 4 shows a schematic of 0.762 mm I.D. nozzle. In this case, a 1.0 mm nozzle, as shown in FIG. 3, is joined by means of a reducing coupler (Reducing union Swagelok® SS-200-6-1) to a 0.762 mm ID tube (Port connector Swagelok® SS-101-PC). FIG. 5 shows a schematic of the injection chamber used in the example. In FIG. 5, the body of the injection chamber is stainless steel tube 50, I.D. 9.56 mm, wall thickness 12.7 mm, length 150 mm. This is fitted with reducing connector 51, which connects to chamber 5 (FIG. 1). The other end of tube 50 is fitted with reducing connector 52 (Reducing union Swagelok® SS-810-6-2), with outlet diameter 3.175 mm, adapted to receive the nozzle shown in FIG. 4. FIG. 6 shows a schematic of the precipitation chamber used in the example. Precipitation chamber 60 is a 300 ml bolt closure vessel made of stainless steel. It comprises lid, 62 and body 64, which may be sealably bolted together. Lid 62 is fitted with nozzle 8 (see FIG. 1), which extends about 20 mm into the interior of chamber 60. Lid 62 also has port 7' (see FIG. 1) for admitting carbon dioxide, and port 66 adapted to receive pressure transducer P2 (FIG. 1). Stainless steel gasket is provided to seal between lid 62 and body 64 when chamber 60 is closed. Body 64 is provided at the bottom with outlet port 7" for allowing materials (product, fluid, solvent) to leave chamber 60. The overall height of the interior of chamber 60 is 700 mm and the diameter is 46 mm.

FIG. 7 shows photographs of bovine insulin. The left hand photograph shows the insulin before processing, and the right hand photograph shows the same mass of insulin after being formed into particles according to the present invention. The diameter of the vials is about 38 mm. It is clear that the bulk density of the product made by the present process is far lower than the material from which it is produced. FIG. 8 shows electron micrographs of particulate particulate substances produced by the process of the present invention. At different magnifications, the open, loose nature of the aggregates and the homogeneous nature of the particles that comprise the aggregates can be seen.

FIG. 9 shows a particle size analysis report of insulin particles produced by the process of the present invention. Two separate species may be seen, one centred at about is 0.1-0.2 microns and the other at about 1-2 microns. The former represents the primary particles produced in the process, whereas the latter represents the loose aggregates of primary particles.

FIG. 10 shows numerical results of in-vitro inhalability testing of insulin particles produced by the process of the present invention. The graph indicates a simulated distribution of product in the human lung. MMAD is "mass median aerodynamic diameter", and relates to the aerodynamic character of the product. The bars indicate simulated deposition within the human lung, with the right hand bars indicating deposition in the deep lung. The bars paired together indicate results of two separate analyses. FIG. 11 show graphs showing results of inhalability testing with and without device of insulin particles produced by the process of the present invention. In both cases a large proportion of particles have ECD of less than 0.4 microns, indicating that the drugs would be efficiently delivered to the lungs during inhalation. ECD is the Effective Cutoff Diameter, which reflects the aerodynamic character of product during testing. It should be noted that aerodynamic diameters may be quite different to geometrical diameters.

Using procedures based on those outlined above, the following experiments were performed:

1) Hydroxypropylated beta-Cyclodextrin (HP βCD) (FIG. 12)
HP βCD mass: 2000 mg
Methanol volume: 10 ml
Temperature: 40° C.
Precipitation vessel Pre-delivery Pressure: 120 bar
Precipitation vessel Post-delivery Pressure: 136.8 bar In this example, 2000 mg of HP βCD was dissolved in 10 ml methanol to form a working solution. After purging the precipitation chamber 7 of air with $CO_2$ (99.5%—Linde), $CO_2$ was introduced into the precipitation chamber 7 through a spiral heating coil 4 with a syringe pump 3 (ISCO 500D) to the desired working pressure; the chamber 7 was then sealed. Working pressures selected in this study were above the saturation pressure of the $CO_2$/Methanol system. The precipitation chamber 7 was allowed 30 mins to achieve equilibrium. The working solution was next introduced into the injection chamber 6 with a syringe through $V_5$. The injection chamber 6 and back-pressure vessel 5 were then charged with nitrogen (99.999%—Linde) to a pressure 50 bar in excess of the precipitation vessel 7 and sealed. Nitrogen was used to achieve the pressure differential because of its low solubility in the working solution so as to prevent undesirable expansion and precipitation prior to delivery.

By quickly opening $V_6$ for a period of 5 seconds, the working solution was energetically delivered into the precipitation chamber 7 through the 3.2 mm tubing 8. Upon opening $V_6$, the injection chamber 6 experienced an abrupt depressurization as its contents were emptied into the precipitation vessel 7 almost instantaneously. The pressure of the precipitation chamber 7 experienced a simultaneous increase. The contents of the precipitation chamber 7 were then allowed to rest for 10 minutes to achieve a stable pressure. $CO_2$ was next passed through the precipitation chamber 7 under isobaric and isothermal conditions to flush the system of Methanol. Precipitate was retained in the precipitation chamber 7 with a 0.5 micron frit at the base, while allowing extracted solvent and antisolvent to exit the precipitation chamber 7.

2) EUDRAGIT™S100 (poly-(methacrylic acid-co-methyl methacrylate) 1:2) (FIG. 13)
EUDRAGIT™S100 (poly-(methacrylic acid-co-methyl methacrylate) 1:2) mass: 200 mg
Acetone volume: 10 ml
Temperature: 40° C.
Precipitation vessel Pre-delivery Pressure: 120 bar
Precipitation vessel Post-delivery Pressure: 128.8 bar In this example, 200 mg of EUDRAGIT™S100 (poly-(methacrylic acid-co-methyl methacrylate) 1:2) was dissolved in 10 ml acetone. After purging the precipitation chamber 7 of air with $CO_2$ (99.5%—Linde), $CO_2$ was introduced into the precipitation chamber 7 through a spiral heating coil 4 with a syringe pump 3 (ISCO 500D) to the desired working pressure; the chamber 7 was then sealed. Working pressures selected in this study were above the saturation pressure of the $CO_2$/acetone system. The precipitation chamber 7 was allowed 30 mins to achieve equilibrium. The working solution was next introduced into the injection chamber 6 with a syringe through $V_5$. The injection chamber 6 and back-pressure vessel 5 were then charged with nitrogen (99.999%—Linde) to a pressure 50 bar in excess of the precipitation vessel 7 and sealed. Nitrogen was used to achieve the pressure differential because of its low solubility in the working solution so as to prevent undesirable expansion and precipitation prior to delivery.

By quickly opening $V_6$ for a period of 5 seconds, the working solution was energetically delivered into the precipitation chamber 7 through the 3.2 mm tubing 8. Upon opening $V_6$, the injection chamber 6 experienced an abrupt depressurization as its contents were emptied into the precipitation vessel 7 almost instantaneously. The pressure of the precipitation chamber 7 experienced a simultaneous increase. The contents of the precipitation chamber 7 were then allowed to rest for 10 minutes to achieve a stable pressure. $CO_2$ was next passed through the precipitation chamber 7 under isobaric and isothermal conditions to flush the system of acetone. Precipitate was retained in the precipitation chamber 7 with a 0.5 micron frit at the base, while allowing extracted solvent and antisolvent to exit the precipitation chamber 7.

3) Iron Oxide ($Fe_3O_4$) Encapsulated with Hydroxypropylated beta-Cyclodextrin (HP βCD) (FIGS. 14 and 15)
HP βCD mass: 1000 mg
$Fe_3O_4$ mass: 60 mg
Methanol volume: 10 ml
Temperature: 40° C.
Precipitation vessel Pre-delivery Pressure: 120 bar
Precipitation vessel Post-delivery Pressure: 138.7 bar In this example, 60 mg of $Fe_3O_4$ was added to 1000 mg of HP βCD and 10 ml of methanol was next added to the powder mixture. HP βCD dissolved into Methanol while $Fe_3O_4$ remained undissolved. After purging the precipitation chamber 7 of air with $CO_2$ (99.5%—Linde), $CO_2$ was introduced into the precipitation chamber 7 through a spiral heating coil 4 with a syringe pump 3 (ISCO 500D) to the desired working pressure; the chamber 7 was then sealed. Working pressures selected in this study were above the saturation pressure of the $CO_2$/methanol system. The precipitation chamber 7 was allowed 30 mins to achieve equilibrium. The working suspension comprising of HP βCD dissolved in methanol and $Fe_3O_4$ in suspension was next introduced into the injection chamber 6 with a syringe through $V_5$. The injection chamber 6 and back-pressure vessel 5 were then charged with nitrogen (99.999%—Linde) to a pressure 50 bar in excess of the precipitation vessel 7 and sealed. Nitrogen was used to achieve the pressure differential because of its low solubility in the working suspension so as to prevent undesirable expansion and precipitation prior to delivery.

By quickly opening $V_6$ for a period of 5 seconds, the working suspension was energetically delivered into the precipitation chamber 7 through the 3.2 mm tubing 8. Upon opening $V_6$, the injection chamber 6 experienced an abrupt depressurization as its contents were emptied into the precipitation vessel 7 almost instantaneously. The pressure of the precipitation chamber 7 experienced a simultaneous increase. The contents of the precipitation chamber 7 were then allowed to rest for 10 minutes to achieve a stable pressure. $CO_2$ was next passed through the precipitation chamber 7 under isobaric and isothermal conditions to flush the system of methanol. Precipitate was retained in the precipitation chamber 7 with a 0.5 micron frit at the base, while allowing extracted solvent and antisolvent to exit the precipitation chamber 7.

Figure 14:
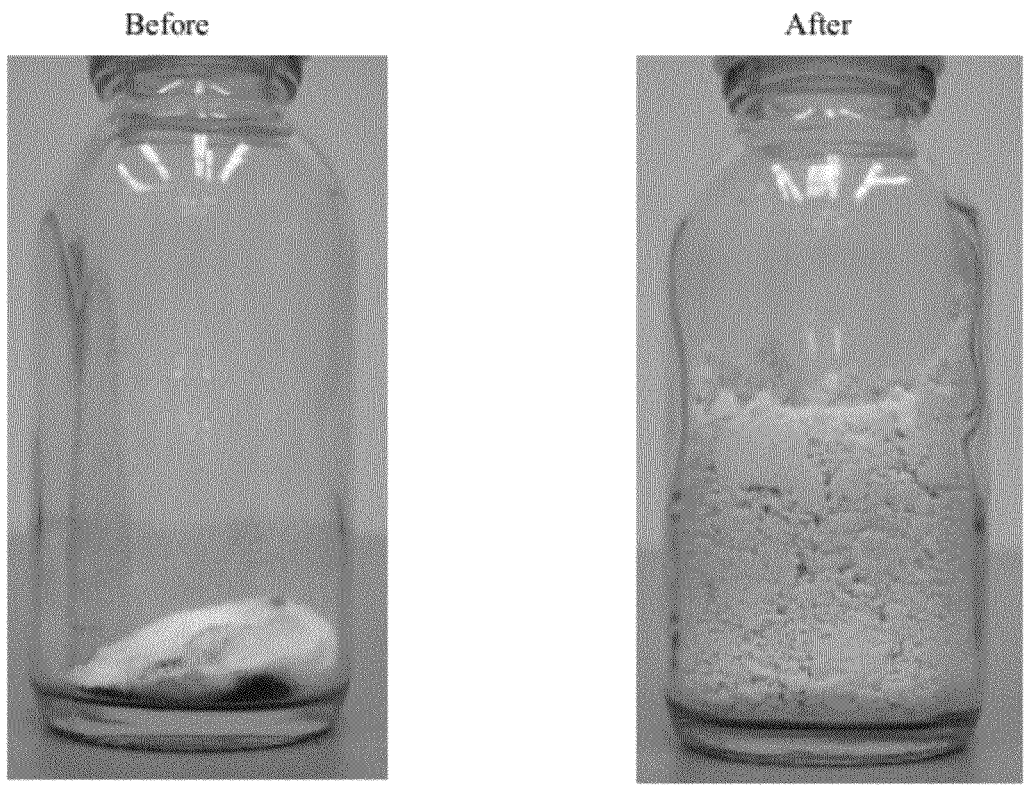
FIG. 14 shows photographs of: (before) mixed iron oxide ($Fe_3O_4$) and hydroxypropylated beta-cyclodextrin (HP βCD); and (after) iron oxide encapsulated with HP βCD.

From FIGS. 12 to 14 it can be seen that the process of the present invention provides in each case a lighter, fluffier material with a far lower bulk density ("after") than its precursor substance ("before"). FIG. 15 illustrates the magnetic properties of the particles produced using a magnetic substance as a precursor. Thus in FIG. 15, the particles having a magnetic core are attracted to the magnet at the top of the container, showing that the magnetic core particles have indeed been encapsulated.

The invention claimed is:

1. A process for producing particles of a substance comprising the steps of:
    delivering a solution of the substance in a solvent through conduit at a flow rate of at least 1 L/s in at least one shot from an injection chamber into a supercritical fluid disposed in a precipitation chamber, said supercritical fluid being a non-solvent for the substance and being miscible with the solvent, and
    forming particles of the substance, said particles being distributed in a mixture of the solvent and the supercritical fluid.

2. The process of claim 1 wherein the step of delivering comprises delivering the solution in a single shot into the supercritical fluid.

3. The process of claim 1 wherein the step of delivering comprises delivering the solution in more than one shot simultaneously into the supercritical fluid.

4. The process of claim 1 wherein the step of delivering is conducted sufficiently rapidly for the solution to be distributed throughout the supercritical fluid following said delivering.

5. The process of claim 1 wherein the step of delivering is conducted with a flow rate of the solution into the supercritical fluid of between about 1 and about 100 L/s.

6. The process of claim 1 additionally comprising the step of pressurizing the solution with a gas to a pressure greater than that of the supercritical fluid before delivering the solution into the supercritical fluid, said gas having solubility in the solution of less than 10% v/v.

7. The process of claim 1 comprising pressurizing the solution to a pressure at least about 20 bar greater than the pressure of the supercritical fluid before delivering the solution into the supercritical fluid.

8. The process of claim 1 wherein the process of delivering comprises opening an injection valve so as to permit the solution to combine with the supercritical fluid.

9. The process of claim 1 wherein the step of forming consists of forming the particles throughout the mixture of the solvent and the supercritical fluid.

10. The process of claim 1 additionally comprising separating the particles from the mixture of the solvent and the supercritical fluid.

11. The process of claim 10 wherein said separating is conducted while maintaining said mixture in its supercritical state.

12. The process of claim 10 additionally comprising washing the particles with the supercritical fluid.

13. The process of claim 10 additionally comprising depressurizing the particles to ambient pressure after said separating.

14. The process of claim 1 wherein the supercritical fluid comprises supercritical carbon dioxide.

15. The process of claim 1 wherein the substance is a pharmaceutically active substance.

16. The process of claim 1 wherein the substance is selected from the group consisting of insulin, hydroxypropylated beta-cyclodextrin, Budesonide, EUDRAGIT™ S100 (poly-(methacrylic acid-co-methyl methacrylate)1:2), lidocaine, adenosine, dobutamine, dopamine, epinephrine, norepinephrine, phentolamine, doxapram, alfentanil, dezocin, nalbuphine, buprenorphine, naloxone, ketorolac, midazolam, propofol, metacurine, mivacurium, succinylcholine, methicillin, mezlocillin, piperacillin, cetoxitin, cefonicid, cefmetazole and aztreonam, or any combination thereof.

17. The process of claim 1 wherein the solution comprises core particles, whereby the particles of the substance comprise the core particles at least partially coated with the substance.

18. The process of claim 1 additionally comprising the steps of:
    delivering a solution of a second substance in a second solvent in at least one shot into the supercritical fluid, said supercritical fluid being a non-solvent for the second substance and being miscible with the second solvent, and
    forming at least partially coated particles comprising the particles of the substance at least partially coated by the second substance, said at least partially coated particles being distributed in a mixture of the solvent, the second solvent and the supercritical fluid.

* * * * *

UNITED STATES PATENT AND TRADEMARK OFFICE
CERTIFICATE OF CORRECTION

PATENT NO. : 8,389,013 B2
APPLICATION NO. : 12/444490
DATED : March 5, 2013
INVENTOR(S) : Neil Russell Foster and Roderick Peng Tze Sih It is certified that error appears in the above-identified patent and that said Letters Patent is hereby corrected as shown below:

In the Claims

Claim 1, Column 33, line 14, before "conduit at a flow rate," insert --a--.

Signed and Sealed this
Fourth Day of November, 2014

Michelle K. Lee
*Deputy Director of the United States Patent and Trademark Office*